US011291842B2

(12) United States Patent
Caparso et al.

(10) Patent No.: US 11,291,842 B2
(45) Date of Patent: Apr. 5, 2022

(54) SYSTEMS AND METHODS FOR IMPROVING SLEEP DISORDERED BREATHING

(71) Applicant: XII Medical, Inc., Cleveland, OH (US)

(72) Inventors: Anthony V. Caparso, North Ridgeville, OH (US); Josh Nickols, Louisville, KY (US)

(73) Assignee: XII Medical, Inc., Cleveland, OH (US)

( * ) Notice: Subject to any disclaimer, the term of this patent is extended or adjusted under 35 U.S.C. 154(b) by 126 days.

(21) Appl. No.: 16/866,523

(22) Filed: May 4, 2020

(65) Prior Publication Data

US 2020/0346017 A1 Nov. 5, 2020

Related U.S. Application Data

(60) Provisional application No. 62/841,978, filed on May 2, 2019.

(51) Int. Cl.
*A61N 1/36* (2006.01)
*A61N 1/05* (2006.01)
(Continued)

(52) U.S. Cl.
CPC ....... *A61N 1/36139* (2013.01); *A61N 1/0548* (2013.01); *A61N 1/3611* (2013.01);
(Continued)

(58) Field of Classification Search
CPC ............. A61N 1/36139; A61N 1/0548; A61N 1/3611; A61N 1/37229; A61B 5/1114; A61B 5/1116
See application file for complete search history.

(56) References Cited

U.S. PATENT DOCUMENTS

| 4,990,160 A | 2/1991 | Terino |
| 5,591,216 A | 1/1997 | Testerman et al. |

(Continued)

FOREIGN PATENT DOCUMENTS

| JP | 2013-208182 A | 10/2013 |
| WO | 1992/19318 A1 | 11/1992 |

(Continued)

OTHER PUBLICATIONS

Bailey, E. Fiona. "Activities of human genioglossus motor units." Respiratory physiology & neurobiology 179.1 (2011): 14-22.
(Continued)

*Primary Examiner* — Amanda K Hulbert
*Assistant Examiner* — Philip C Edwards
(74) *Attorney, Agent, or Firm* — Fortem IP LLP; Katrina Marcelo; Mary Fox

(57) ABSTRACT

A neuromodulation system is provided herein. The system can include a neuromodulation device, an electronics package, which can be part of the neuromodulation device; an external controller; a sensor; and a computing device. The neuromodulation device can include a neuromodulation lead having a lead body configured to be bent to a desired shape and to maintain that shape in order to position the electrodes relative to neural and/or muscular structures when fully deployed. The neuromodulation device can also include an antenna including an upper and a lower coil electrically connected to each other in parallel. The computing device can execute a closed-loop algorithm based on physiological sensed data relating to sleep.

19 Claims, 10 Drawing Sheets

(51) Int. Cl.
*A61N 1/372* (2006.01)
*A61B 5/11* (2006.01)
*A61B 5/00* (2006.01)
*A61B 5/394* (2021.01)

(52) U.S. Cl.
CPC ......... *A61N 1/37229* (2013.01); *A61B 5/1114* (2013.01); *A61B 5/1116* (2013.01); *A61B 5/394* (2021.01); *A61B 5/4552* (2013.01); *A61B 5/4812* (2013.01); *A61B 5/4818* (2013.01); *A61N 1/37211* (2013.01)

(56) References Cited

U.S. PATENT DOCUMENTS

| | | | |
|---|---|---|---|
| 5,609,621 A | 3/1997 | Bonner | |
| 5,716,377 A | 2/1998 | Rise et al. | |
| 5,877,466 A | 3/1999 | Bolongeat-Mobleu et al. | |
| 5,988,171 A | 11/1999 | Sohn et al. | |
| 6,240,316 B1 | 5/2001 | Richmond et al. | |
| 6,587,725 B1 | 7/2003 | Durand et al. | |
| 6,770,022 B2 | 8/2004 | Mechlenburg et al. | |
| 7,660,632 B2 | 2/2010 | Kirby et al. | |
| 7,668,591 B2 | 2/2010 | Lee et al. | |
| 7,711,438 B2 | 5/2010 | Lattner et al. | |
| 7,885,713 B2 | 2/2011 | Campbell et al. | |
| 8,255,056 B2 | 8/2012 | Tehrani | |
| 8,498,712 B2 | 7/2013 | Bolea et al. | |
| 8,498,713 B2 | 7/2013 | McClure et al. | |
| 8,574,164 B2 | 11/2013 | Mashiach | |
| 8,577,464 B2 | 11/2013 | Mashiach | |
| 8,577,465 B2 | 11/2013 | Mashiach | |
| 8,577,466 B2 | 11/2013 | Mashiach | |
| 8,577,467 B2 | 11/2013 | Mashiach et al. | |
| 8,577,468 B2 | 11/2013 | Mashiach et al. | |
| 8,577,472 B2 | 11/2013 | Mashiach et al. | |
| 8,577,478 B2 | 11/2013 | Mashiach et al. | |
| 8,577,647 B2 | 11/2013 | Farritor et al. | |
| 8,585,617 B2 | 11/2013 | Mashiach et al. | |
| 8,588,941 B2 | 11/2013 | Mashiach | |
| 8,626,304 B2 | 1/2014 | Bolea et al. | |
| 8,644,957 B2 | 2/2014 | Mashiach | |
| 8,700,183 B2 | 4/2014 | Mashiach | |
| 8,718,776 B2 | 5/2014 | Mashiach et al. | |
| 8,744,589 B2 | 6/2014 | Bolea et al. | |
| 8,751,005 B2 | 6/2014 | Meadows et al. | |
| 8,798,773 B2 | 8/2014 | Mashiach | |
| 8,812,113 B2 | 8/2014 | Mashiach | |
| 8,812,135 B2 | 8/2014 | Mashiach | |
| 8,831,730 B2 | 9/2014 | Mashiach et al. | |
| 8,838,256 B2 | 9/2014 | Mashiach et al. | |
| 8,897,880 B2 | 11/2014 | Mashiach | |
| 8,897,895 B2 | 11/2014 | Mashiach | |
| 8,903,493 B2 | 12/2014 | Mashiach et al. | |
| 8,903,515 B2 | 12/2014 | Mashiach | |
| 8,948,871 B2 | 2/2015 | Mashiach et al. | |
| 8,958,893 B2 | 2/2015 | Mashiach | |
| 8,989,868 B2 | 3/2015 | Mashiach et al. | |
| 9,031,653 B2 | 5/2015 | Mashiach | |
| 9,031,654 B2 | 5/2015 | Meadows et al. | |
| 9,044,612 B2 | 6/2015 | Mashiach et al. | |
| 9,061,151 B2 | 6/2015 | Mashiach et al. | |
| 9,061,162 B2 | 6/2015 | Mashiach et al. | |
| 9,095,725 B2 | 8/2015 | Mashiach | |
| 9,101,774 B2 | 8/2015 | Mashiach et al. | |
| 9,155,899 B2 | 10/2015 | Mashiach et al. | |
| 9,186,511 B2 | 11/2015 | Bolea | |
| 9,220,907 B2 | 12/2015 | Mashiach et al. | |
| 9,220,908 B2 | 12/2015 | Mashiach | |
| 9,248,290 B2 | 2/2016 | Mashiach | |
| 9,248,291 B2 | 2/2016 | Mashiach | |
| 9,248,302 B2 | 2/2016 | Mashiach et al. | |
| 9,259,585 B2 | 2/2016 | Vajha et al. | |
| 9,302,093 B2 | 4/2016 | Mashiach | |
| 9,308,370 B2 | 4/2016 | Lima et al. | |
| 9,308,381 B2 | 4/2016 | Mashiach et al. | |
| 9,314,613 B2 | 4/2016 | Mashiach | |
| 9,314,641 B2 | 4/2016 | Meadows et al. | |
| 9,327,132 B2 | 5/2016 | Mashiach | |
| 9,339,651 B2 | 5/2016 | Meadows et al. | |
| 9,358,392 B2 | 6/2016 | Mashiach | |
| 9,370,657 B2 | 6/2016 | Tehrani et al. | |
| 9,393,435 B2 | 7/2016 | Mashiach | |
| 9,403,009 B2 | 8/2016 | Mashiach | |
| 9,403,025 B2 | 8/2016 | Mashiach et al. | |
| 9,409,013 B2 | 8/2016 | Mashiach et al. | |
| 9,415,215 B2 | 8/2016 | Mashiach | |
| 9,415,216 B2 | 8/2016 | Mashiach | |
| 9,421,372 B2 | 8/2016 | Mashiach et al. | |
| 9,463,318 B2 | 10/2016 | Mashiach et al. | |
| 9,486,628 B2 | 11/2016 | Christopherson et al. | |
| 9,757,560 B2 | 9/2017 | Papay | |
| 9,849,288 B2 | 12/2017 | Meadows et al. | |
| 9,950,166 B2 | 4/2018 | Mashiach et al. | |
| 10,029,098 B2 | 7/2018 | Papay | |
| 10,065,038 B2 * | 9/2018 | Papay | A61N 1/3787 |
| 10,105,538 B2 | 10/2018 | Bolea et al. | |
| 10,238,468 B2 | 3/2019 | Forsell | |
| 10,675,467 B2 | 6/2020 | Papay | |
| 2002/0010495 A1 | 1/2002 | Freed et al. | |
| 2004/0122787 A1 | 6/2004 | Avinash et al. | |
| 2006/0224211 A1 | 10/2006 | Durand et al. | |
| 2007/0160274 A1 | 7/2007 | Mashiach | |
| 2007/0263915 A1 | 11/2007 | Mashiach | |
| 2008/0260229 A1 | 10/2008 | Mashiach | |
| 2009/0082831 A1 | 3/2009 | Paul et al. | |
| 2009/0226057 A1 | 9/2009 | Mashiach et al. | |
| 2009/0270960 A1 | 10/2009 | Zhao et al. | |
| 2010/0094379 A1 | 4/2010 | Meadows et al. | |
| 2010/0179562 A1 | 7/2010 | Linker et al. | |
| 2010/0241195 A1 | 9/2010 | Meadows et al. | |
| 2010/0260217 A1 | 10/2010 | Redford | |
| 2010/0280568 A1 | 11/2010 | Bulkes et al. | |
| 2010/0292769 A1 | 11/2010 | Brounstein et al. | |
| 2011/0071606 A1 | 3/2011 | Kast et al. | |
| 2011/0093036 A1 | 4/2011 | Mashiach | |
| 2011/0230702 A1 | 9/2011 | Honour | |
| 2012/0010532 A1 | 1/2012 | Bolea et al. | |
| 2013/0085537 A1 | 4/2013 | Mashiach | |
| 2013/0085558 A1 | 4/2013 | Mashiach | |
| 2013/0204097 A1 | 8/2013 | Rondoni et al. | |
| 2013/0289401 A1 | 10/2013 | Colbaugh et al. | |
| 2014/0031840 A1 | 1/2014 | Mashiach | |
| 2014/0031902 A1 | 1/2014 | Mashiach | |
| 2014/0031903 A1 | 1/2014 | Mashiach | |
| 2014/0031904 A1 | 1/2014 | Mashiach | |
| 2014/0046221 A1 | 2/2014 | Mashiach et al. | |
| 2014/0052219 A1 | 2/2014 | Mashiach et al. | |
| 2014/0100642 A1 | 4/2014 | Mashiach | |
| 2014/0135868 A1 | 5/2014 | Bashyam | |
| 2014/0172061 A1 | 6/2014 | Mashiach | |
| 2014/0266933 A1 | 9/2014 | Andersen et al. | |
| 2014/0358026 A1 | 12/2014 | Mashiach et al. | |
| 2014/0358189 A1 | 12/2014 | Mashiach et al. | |
| 2014/0358196 A1 | 12/2014 | Mashiach | |
| 2014/0358197 A1 | 12/2014 | Mashiach et al. | |
| 2014/0371802 A1 | 12/2014 | Mashiach et al. | |
| 2014/0371817 A1 | 12/2014 | Mashiach et al. | |
| 2014/0379049 A1 | 12/2014 | Mashiach et al. | |
| 2015/0032177 A1 | 1/2015 | Mashiach et al. | |
| 2015/0073232 A1 | 3/2015 | Ahmad et al. | |
| 2015/0077308 A1 | 3/2015 | Jeon et al. | |
| 2015/0088025 A1 | 3/2015 | Litvak et al. | |
| 2015/0096167 A1 | 4/2015 | Zhao et al. | |
| 2015/0112402 A1 | 4/2015 | Mashiach | |
| 2015/0112416 A1 | 4/2015 | Mashiach et al. | |
| 2015/0142120 A1 | 5/2015 | Papay | |
| 2015/0224307 A1 | 8/2015 | Bolea | |
| 2015/0265221 A1 | 9/2015 | Flanagan et al. | |
| 2015/0283313 A1 | 10/2015 | Huber | |
| 2015/0290454 A1 | 10/2015 | Tyler et al. | |
| 2015/0290465 A1 | 10/2015 | Mashiach | |
| 2015/0343221 A1 | 12/2015 | Mashiach | |
| 2016/0094082 A1 | 3/2016 | Ookawa et al. | |
| 2016/0106976 A1 | 4/2016 | Kucklick | |

(56) References Cited

U.S. PATENT DOCUMENTS

| | | |
|---|---|---|
| 2016/0121121 A1 | 5/2016 | Mashiach |
| 2016/0121122 A1 | 5/2016 | Mashiach |
| 2016/0175587 A1 | 6/2016 | Lima et al. |
| 2016/0184583 A1 | 6/2016 | Meadows et al. |
| 2016/0235990 A1 | 8/2016 | Mashiach |
| 2016/0346537 A1 | 12/2016 | Mashiach |
| 2017/0087360 A1 | 3/2017 | Scheiner |
| 2017/0128002 A1 | 5/2017 | Christopherson et al. |
| 2017/0143230 A1 | 5/2017 | Kent et al. |
| 2017/0290699 A1 | 10/2017 | Radmand |
| 2017/0296815 A1* | 10/2017 | Papay ................ A61N 1/37223 |
| 2018/0015282 A1 | 1/2018 | Waner et al. |
| 2018/0028824 A1 | 2/2018 | Pivonka et al. |
| 2018/0117313 A1 | 5/2018 | Schmidt et al. |
| 2018/0191069 A1 | 7/2018 | Chen et al. |
| 2018/0200512 A1 | 7/2018 | Bolea et al. |
| 2018/0221673 A1 | 8/2018 | Kuang |
| 2019/0151656 A1 | 5/2019 | Bolea et al. |
| 2019/0160282 A1 | 5/2019 | Dieken et al. |
| 2019/0247664 A1 | 8/2019 | Irazoqui et al. |
| 2020/0016401 A1 | 1/2020 | Papay et al. |
| 2020/0254249 A1 | 8/2020 | Rondoni et al. |
| 2020/0269044 A1 | 8/2020 | Papay |
| 2020/0346010 A1 | 11/2020 | Papay et al. |
| 2020/0346016 A1 | 11/2020 | Caparso et al. |
| 2020/0346024 A1 | 11/2020 | Caparso et al. |
| 2021/0106824 A1 | 4/2021 | Caparso et al. |
| 2021/0128914 A1 | 5/2021 | Papay |

FOREIGN PATENT DOCUMENTS

| | | |
|---|---|---|
| WO | 2005/018737 A1 | 3/2005 |
| WO | WO-2007/080579 A2 | 7/2007 |
| WO | WO-2007/080580 A2 | 7/2007 |
| WO | WO-2008/129545 A1 | 10/2008 |
| WO | WO-2009/007896 A2 | 1/2009 |
| WO | WO-2009/109971 A2 | 9/2009 |
| WO | 2009/143560 A1 | 12/2009 |
| WO | 2010/006218 A2 | 1/2010 |
| WO | WO-2011/048590 A1 | 4/2011 |
| WO | WO-2011/077433 A1 | 6/2011 |
| WO | WO-2013/046032 A2 | 4/2013 |
| WO | WO-2013/046035 A2 | 4/2013 |
| WO | WO-2013/046038 A2 | 4/2013 |
| WO | WO-2013/046039 A2 | 4/2013 |
| WO | WO-2013/046040 A2 | 4/2013 |
| WO | WO-2013/046042 A2 | 4/2013 |
| WO | WO-2013/046043 A2 | 4/2013 |
| WO | WO-2013/046044 A2 | 4/2013 |
| WO | WO-2013/046048 A2 | 4/2013 |
| WO | WO-2013/046049 A2 | 4/2013 |
| WO | WO-2013/046053 A2 | 4/2013 |
| WO | WO-2013/057594 A2 | 4/2013 |
| WO | WO-2013/061164 A2 | 5/2013 |
| WO | WO-2013/061169 A2 | 5/2013 |
| WO | 2013/177621 A1 | 12/2013 |
| WO | WO-201 4/016687 A2 | 1/2014 |
| WO | WO-2014/016684 A2 | 1/2014 |
| WO | WO-2014/016686 A2 | 1/2014 |
| WO | WO-2014/016688 A2 | 1/2014 |
| WO | WO-2014/016691 A2 | 1/2014 |
| WO | WO-2014/016692 A2 | 1/2014 |
| WO | WO-2014/016693 A2 | 1/2014 |
| WO | WO-2014/016694 A2 | 1/2014 |
| WO | WO-2014/016697 A2 | 1/2014 |
| WO | WO-2014/016700 A2 | 1/2014 |
| WO | WO-2014/016701 A2 | 1/2014 |
| WO | 2014/047310 A1 | 3/2014 |
| WO | WO-2014/049448 A2 | 4/2014 |
| WO | WO-2014/057361 A2 | 4/2014 |
| WO | WO-2014/096969 A2 | 6/2014 |
| WO | WO-2014/096971 A1 | 6/2014 |
| WO | WO-2014/096973 A2 | 6/2014 |
| WO | WO-2014/207576 A2 | 12/2014 |
| WO | WO-2015/004540 A2 | 1/2015 |
| WO | 2015/139053 A1 | 9/2015 |

OTHER PUBLICATIONS

PCT International Search Report and Written Opinion for corresponding International Application Serial No. PCT/US2020/031383, dated Oct. 9, 2020, pp. 1-17.

PCT International Search Report and Written Opinion for corresponding International Application Serial No. PCT/US2020/031389, dated Sep. 8, 2020, pp. 1-12.

Bjorninen, T. et al. (2009). "The effect of fabrication method on passive UHF RFID tag performance," International Journal of Antennas and Propagation, vol. 2009, Article ID 920947, pp. 1-8.

Cienfuegos et al., Mandible—Surgical approach—Intraocular—AO Surgery Reference, v1 .0 Dec. 1, 2008 (Accessed Apr. 18, 2016).

Cienfuegos et al., Mandible—Surgical approach—Submental—AO Surgery Reference, v1 .0 Dec. 1, 2008 (Accessed Apr. 18, 2016).

European Office Action corresponding to EP Application No. 14 809 219.0, dated May 2, 2017, 4 pages.

Final Office Action dated Jan. 10, 2017, for U.S. Appl. No. 14/547,400, filed Nov. 19, 2014, 14 pages.

Finai Office Action dated Jun. 20, 2018, for U.S. Appl. No. 15/618,199, filed on . Jun. 9, 2017, 10 pages.

Final Office Action dated Apr. 23, 2019, for U.S. Appl. No. 15/618,199, filed Jun. 9, 2017, 9 pages.

Final Office Action dated Oct. 23, 2020, for U.S. Appl. No. 16/865,668, filed May 4, 2020, 14 pages.

Final Office Action dated Dec. 22, 2020, for U.S. Appl. No. 16/618,199, filed May 4, 2020, 16 pages.

IFinai Office Action dated Feb. 7, 2018, for U.S. Appl. No. 15/341,039, filed Nov. 2, 2016, 16 pages.

Final Office Action dated Aug. 17, 2021, for U.S. Appl. No. 16/865,668, filed May 4, 2020, 7 pages.

Final Office Action mailed on Jul. 27, 2021, for U.S. Appl. No. 16/507,390, filed on 182 Jul. 10, 2019, 13 pages.

Final Office Action dated Oct. 15, 2021, for U.S. Appl. No. 16/865,541, filed May 4, 2020, 18 pages.

Finai Office Action dated Nov. 22, 2021, for U.S. Appl. No. 16/865,363, filed on May 3, 2020, 9 pages.

International Search Report and Written Opinion dated Feb. 10, 2015, for PCT Application No. PCT/US2014/066311, filed on Nov. 19, 2014, 8 pages.

International Search Report and Written Opinion dated Sep. 7, 2020, for PCT Application No. PCT/US2020/031266, filed on May 4, 2020, 10 pages.

International Search Report and Written Opinion dated Aug. 14, 2020, for PCT Application No. PCT/US2020/031279, filed on May 4, 2020, 19 pages.

Non-Final Office Acton dated Apr. 26, 2016, for U.S. Appl. No. 14/547,400, filed Nov. 19, 2014, 12 pages.

Non-Final Office Action dated Aug. 10, 2017, for U.S. Appl. No. 15/341,039, filed on Nov. 2, 2016, 14 pages.

Non-Final Office Action dated Jan. 24, 2018, for U.S. Appl. No. 15/618,199, filed Jun. 9, 2017, 10 pages.

Non-Final Office Action dated Jan. 18, 2019, for U.S. Appl. No. 15/618,199, filed on Jun. 9, 2017, 9 pages.

Non-Final Office Action dated Sep. 26, 2019, for U.S. Appl. No. 15/618,199, filed Jun. 9, 2017, 13 pages.

Non-Final Office Action dated Jun. 24, 2020, for U.S. Appl. No. 16/865,541, filed May 4, 2020, 14 pages.

Non-Final Office Action dated Jan. 26, 2018, for U.S. Appl. No. 15/639,300, filed on Jun. 30, 2017, 14 pages.

Non-Final Office Action dated Jan. 14, 2021, for U.S. Appl. No. 16/507,390, 195, filed on Jul. 10, 2019, 11 pages.

Non-Final Office Action dated Apr. 16, 2021, for U.S. Appl. No. 16/865,668, filed on May 4, 2020, 8 pages.

Non-Final Office Action dated May 11, 2021, for U.S. Appl. No. 16/865,363, filed May 3, 2020, 10 pages.

Non-Final Office Action dated Jun. 24, 2021, for U.S. Appl. No. 16/865,541, filed on May 4, 2020, 17 pages.

(56) References Cited

OTHER PUBLICATIONS

Non-Final Office Action dated Jul. 15, 2021, for U.S. Appl. No. 16/870,292, filed on May 8, 2020, 5 pages.
Non-Final Office Action dated Sep. 24, 2021, for U.S. Appl. No. 16/866,488, filed on May 4, 2020, 12 pages.
Notice of Allowance dated May 17, 2017, for U.S. Appl. No. 14/547.400, filed on Nov. 19, 2014, 6 pages.
Notice of Allowance dated Apr. 5, 2018, for U.S. Appl. No. 15/341,039, filed on Nov. 2, 2016, 9 pages.
Notice of Allowance dated Jan. 29, 2020, for U.S. Appl. No. 15/618,199, filed Jun. 9, 2017, 8 pages.
Notice of Allowance dated May 10, 2018, for U.S. Appll. No. 15/639,300, filed on Jun. 30, 2017, 8 pages.
Schwartz, A.R et al. (1996). "Electrical stimulation of the lingual musculature in obstructive sleep apnea." Journal of Applied Physiology 81:643-652.

* cited by examiner

SYSTEMS AND METHODS FOR IMPROVING SLEEP DISORDERED BREATHING

CROSS-REFERENCE TO RELATED APPLICATIONS

This application claims the benefit of U.S. Provisional Application Ser. No. 62/841,978, filed May 2, 2019, the disclosure of which is hereby incorporated by reference in its entirety.

TECHNICAL FIELD

An electrical stimulation system for improving sleep disordered breathing is provided.

BACKGROUND

Obstructive sleep apnea (OSA) is the most common type of sleep apnea and is characterized by repeated episodes of complete or partial obstructions of the upper airway during sleep, despite the effort to breathe, and is usually associated with a reduction in blood oxygen saturation. Individuals with OSA are rarely aware of difficulty breathing, even upon awakening. It is often recognized as a problem by others who observe the individual during episodes or is suspected because of its effects on the body. OSA is commonly accompanied with snoring. OSA can be associated with symptoms during the daytime (e.g. excessive daytime sleepiness, decreased cognitive functions). Symptoms may be present for years or even decades without identification, during which time the individual may become conditioned to the daytime sleepiness and fatigue associated with significant levels of sleep disturbance. Individuals who generally sleep alone are often unaware of the condition, without a regular bed-partner to notice and make them aware of the signs.

The most widely used current therapeutic intervention for treating OSA is positive airway pressure whereby a breathing machine pumps a controlled stream of air through a mask worn over the nose, mouth, or both. The additional pressure holds open the relaxed muscles. There are several mechanisms for treating OSA with positive airway pressure therapy. The most common treatment involves the use of continuous positive airway pressure (CPAP) machines. CPAP machines are worn by the OSA patient at nighttime during sleep, with the patient wearing a mask connected by hose to an air pump that maintains positive airway pressure.

Neurostimulation therapy can be an alternative for patients who cannot use a continuous positive airway pressure device. One neurostimulation system senses respiration and deliver mild electrical stimulation to the hypoglossal nerve (HGN) in order to increase muscle tone at the back of the tongue so it will not collapse over the airway. The HGN innervates the tongue musculature. It provides motor control for the muscles of the tongue and helps with important voluntary and involuntary functions like swallowing, speaking, and mastication. Stimulating the HGN can restore the tone to key tongue muscles that, when relaxed, can lead to obstructive sleep apnea.

Conventional HGN neurostimulation systems utilize stimulation leads implanted in the patient's neck/throat, with electrodes touching, e.g., a cuff electrode that surrounds the HGN or in close proximity to the HGN. The leads are connected via wire to a pulse generator implanted under the skin in the patient's chest. From time-to-time, the pulse generator is surgically accessed for battery changes. The system includes a handheld patient controller to allow it to be switched on before sleep.

While HGN neurostimulation therapy has proven to be an effective treatment for OSA, the bulk of the conventional systems and the degree of invasiveness in implanting, using, and maintaining the system is undesirable.

SUMMARY

A neuromodulation system is provided herein. In an aspect, a neuromodulation system comprises a neuromodulation device; an electronics package, which can be part of the neuromodulation device; an external controller; a sensor; and a computing device. The neuromodulation device can comprise a neuromodulation lead having a lead body with a right portion, a left portion, and an intermediate portion. A plurality of electrodes can be disposed on the lead body. In particular, a left set of electrodes can be disposed on the left portion of the lead body and a right set of electrodes can be disposed on the right portion of the lead body. At least one of the plurality of electrodes can be a stimulating electrode configured to deliver a stimulation signal to a target site. The lead body can be biased towards a substantially omega shape when the neuromodulation lead is fully deployed and/or the intermediate portion of the lead body can be biased towards an inferior position relative to the left and right electrode sets when the neuromodulation lead is fully deployed. An antenna can be operably coupled to the neuromodulation lead configured to produce an induced current in response to being disposed in an electromagnetic field. The antenna can comprise an upper and a lower coil electrically connected to each other in parallel. The electronics package can comprise electrical components to control the application of a stimulation signal via the stimulating electrode. The external controller can comprise a control unit and a power mat that supports one or more power transmission coils that are excitable to produce an electromagnetic field for inducing electrical current in the antenna to power the neuromodulation lead. The computing device can comprise a non-transitory memory storing instructions and a processor to access the non-transitory memory and execute the instructions to at least monitor the physiological data recorded by the sensor; identify a trigger within the physiological data, wherein the trigger is identified as a biomarker for a condition related to sleep; and apply a rule-based classification to the trigger to determine whether one or more parameters of the stimulation signal should be altered based on the biomarker, the stimulating electrode configured to deliver the stimulation signal to the target site during a period and to alter the one or more parameters of the stimulation signal in response to a signal from the computing device.

DETAILED DESCRIPTION

As used herein with respect to a described element, the terms "a," "an," and "the" include at least one or more of the described element including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As used herein, "stimulate" or "modulate" in the context of neuromodulation includes stimulating or inhibiting neural activity. A "patient" as described herein includes a mammal, such as a human being. By "improving," the patient's medical disorder is better after therapy than before therapy. As used herein, the terms, "inferior," "superior," "cranial," and caudal refer to anatomical planes and directions when the patient is in a standard anatomical position. Similarly, the terms "left" and "right" refer to the position of elements that correspond to the left and right side of a patient's body in a standard anatomical position.

The present disclosure relates to an implantable electrical stimulation system 10, which can be used to provide a variety of electrical therapies, including neuromodulation therapies such as nerve and/or muscle stimulation. Stimulation can induce excitatory or inhibitory neural or muscular activity. Such therapies can be used at various suitable sites within a patient's anatomy. In one example implementation, the system 10 can be used to treat sleep disordered breathing (SDB) including obstructive sleep apnea (OSA) via neuromodulation of the hypoglossal nerve (HGN).

Electrical Stimulator System

Figure 1:
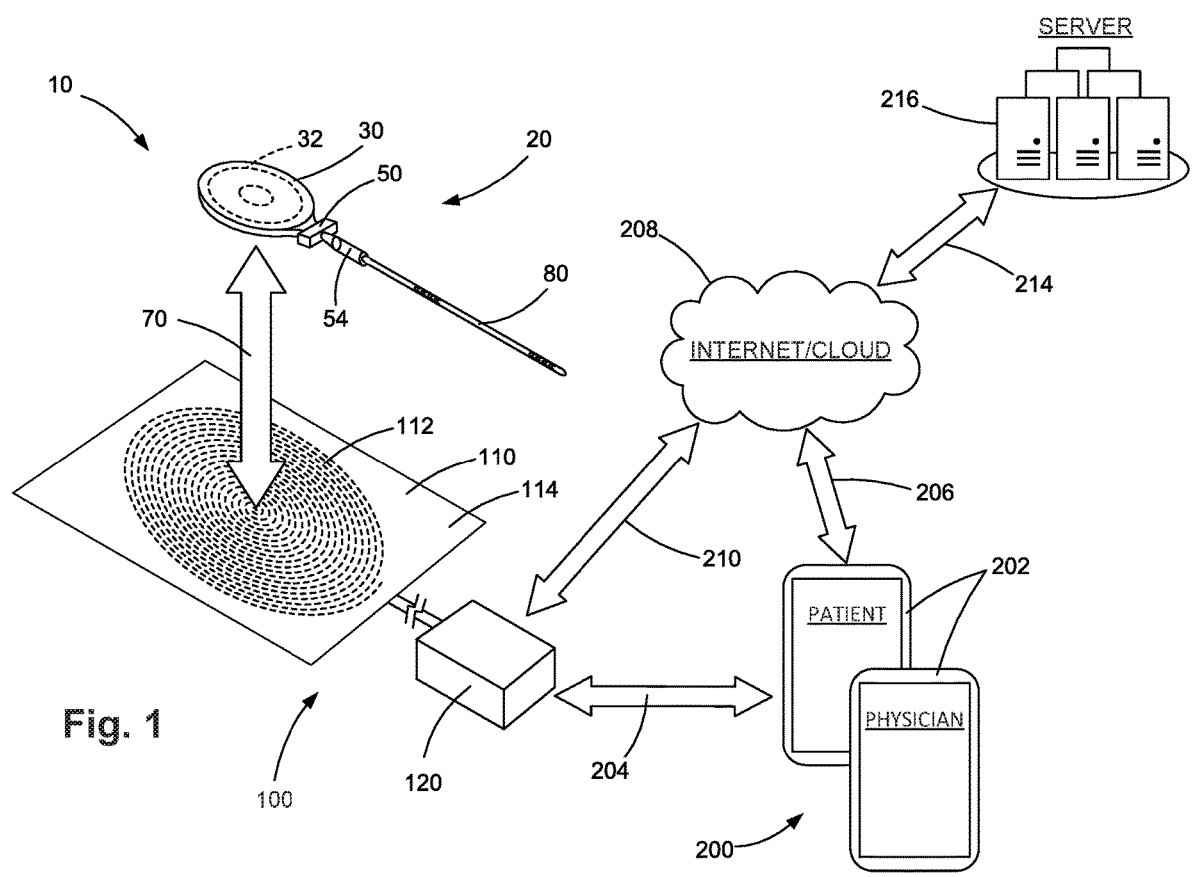
FIG. 1 is a diagram illustrating an example configuration of an implantable stimulation system according to an aspect of the present disclosure.

Referring to FIG. 1, the system 10 can include implantable stimulator 20 (also referred to herein as a "neuromodulation lead") and external controller 100. Controller 100 can power stimulator 20 through electromagnetic induction. Stimulator 20 can include power receiver 30 with antenna 32. Electrical current can be induced in antenna 32 when it is positioned above power mat 112 of controller 100, in an electric field produced by power transmit antenna 112. Antennas 112 and 32 can also facilitate communication between controller 100 and stimulator 20, respectively. This power/communication link between stimulator 20 and controller 100 is shown generally by the arrow 70 in FIG. 1.

System 10 can also include a user interface 200 the form of a computer platform 202 running a custom application that enables communication with controller 100 wirelessly, as indicated generally by arrow 204. This can be done, for example, using Bluetooth or WiFi radio communication. In the example configuration of FIG. 1, computer platform 202 is a smartphone. The type of computer platform 202 could, however, vary. For example, the computer platform 202 can be a physician or patient platform. Each platform 202 can have an application or "app" installed thereon that is user specific, i.e., a patient app or a physician app. The physician platform would have the physician app installed, and the patient platform would have the patient app installed. The patient app can allow the patient to execute certain commands necessary for controlling operation of stimulator 20, such as, for example, start/stop therapy, increase/decrease stimulation power or intensity, and select a stimulation program. In addition to the controls afforded the patient, the physician app can also allow the physician to modify stimulation settings, such as pulse settings (patterns, duration, waveforms, etc.), stimulation frequency, amplitude settings, and electrode configurations, closed-loop and open loop control settings and tuning parameters for the embedded software that controls therapy delivery during use.

As indicated generally by arrow 206, computer platform 202 can be connected (e.g., WiFi and/or LTE) to internet/cloud 208, which facilitates communication 214 with remote or cloud-based server 216. This allows for the transfer of data between server 216 and computer platform 202 via internet 208. Additionally, controller 100 itself can also be internet connected (e.g., WiFi), as shown at 210. This can also allow for the transfer of data between controller 100 and server 216 via internet 208.

System Communication

As shown in FIG. 1 and described above, system 10 can be configured to provide various communication paths between the system components. For example, computer platform 202 being connected to controller 100 (see 204) and to internet 208 (see 206) can facilitate a communication path from remote server 216 (see 214) to stimulator 20 itself (see 70). A communication path between server 216 and stimulator 20 can also be established via WiFi link 210 of controller 100.

Additionally, recognizing that the physician may be remote from the patient, a physician communication path can be established via the internet connection 206 of the remotely located physician platform 202. Through this connection, remote physician platform 202 can communicate with server 216 through internet connection 206. Remote physician platform 202 can also communicate with controller 100, either via internet connection 210 (when enabled) or through patient controller 202.

In addition to facilitating local control of system 10, e.g. controller 100 and stimulator 20, the various communication paths described above can also enable:

Distributing from server 216 software/firmware updates for the computer platform 202, controller 100, and/or stimulator 20.

Downloading from server 216 therapy settings/parameters to be implemented by computer platform 202, controller 100, and/or stimulator 20.

Facilitating therapy setting/parameter adjustments/algorithm adjustments by a remotely located physician.

Uploading data recorded during therapy sessions.

Maintaining coherency in the settings/parameters by distributing changes and adjustments throughout the system components.

System Operation Overview

The therapeutic approach implemented with system 10 can involve implanting only stimulator 20, leaving controller 100 as an external component to be used only during the application of therapy. To facilitate this, stimulator 20 can be configured to be powered by controller 100 through electromagnetic induction. In operation, power mat 110, operated by control unit 120, can be positioned external to the patient in the vicinity of stimulator 20 to position transmitting antenna 112 of the controller, located in the mat, close to receiving antenna 32 of the stimulator. In the implementation where the system 10 is used to treat OSA, the power mat 110 can be positioned on or sufficiently near the sleeping surface while the patient sleeps to maintain the position of the receiving antenna 32 within the target volume of the electromagnetic field generated by the power antenna 112.

Through this approach, system 10 can deliver therapy to improve SDB such as OSA, for example, by stimulating the HGN, for example, through a shorter, less invasive procedure. The elimination of an on-board, implanted power source in favor of an inductive power scheme can eliminate the need for batteries and the associated battery changes over the patient's life.

Additionally, stimulator 20 can implement electromyography (EMG) electrodes for sensing neuromuscular responses to physiological needs of the patient during sleep. Such sensing electrodes can continuously monitor physiological intrinsic EMG signals from the anterior lingual musculature. For instance, EMG sensing electrodes can be configured to detect neuromuscular responses from the genioglossus muscle, which is innervated by the HGN.

Controller 100 can use transmitting antenna 112 for multiple purposes, for example: 1) to provide power to stimulator 20 during therapy sessions, and 2) to communicate with the stimulator. This communication can, for example, include programming, e.g., uploading software/firmware revisions to stimulator 20, changing/adjusting stimulation settings and/or parameters, and adjusting parameters of control algorithms. Controller 100 can receive the programming, software/firmware, and settings/parameters through any of the communication paths described above, e.g., from user interface 200 or through direct WiFi internet connection, when available. The communication paths can also be used to download data from stimulator 20, such as measured data regarding completed stimulation therapy sessions, to the controller 100. The controller 100 can transmit the downloaded data to the user interface 200, which can send/upload the data to server 216 via internet 208.

In operation, sensed EMG responses from the genioglossus muscle can allow closed-loop operation of the stimulator 20 while eliminating the need for a chest lead. Operating in closed-loop, the stimulator 20 can maintain stimulation synchronized with respiration, for example, while preserving the ability to detect and account for momentary obstruction. The stimulator 20 can also detect and respond to snoring, for example.

To facilitate real-time, closed-loop control, a control algorithm can be implemented locally on stimulator 20. This can be achieved, for example, by programming a control algorithm on an application-specific integrated circuit (ASIC) component of stimulator 20 (see below for the description of the stimulator electronics).

Operating in real-time, stimulator 20 can record data related to the stimulation session including, for example, stimulation settings, EMG responses, respiration, sleep state including different stages of REM and non-REM sleep, etc. For example, changes in phasic and tonic EMG activity of genioglossus muscle during inspiration can serve as a trigger for stimulation or changes in stimulation can be made based on changes in phasic and tonic EMG activity of the genioglossus muscle during inspiration or during different sleep stages. After the sleep session, this recorded data can be uploaded to user interface 200 and to server 216. Also, the patient can be queried to use the interface 200 to log data regarding their perceived quality of sleep, which can also be uploaded to the server 216. Offline, the server 216 can execute a software application to evaluate the recorded data to determine whether settings and control parameters can be adjusted to further optimize the stimulation therapy. The software application can, for example, include artificial intelligence (AI) models that, learn from recorded therapy sessions, how certain adjustments affect the therapeutic outcome for the patient. In this manner, through AI learning, the model can provide patient-specific optimized therapy.

Figure 11:
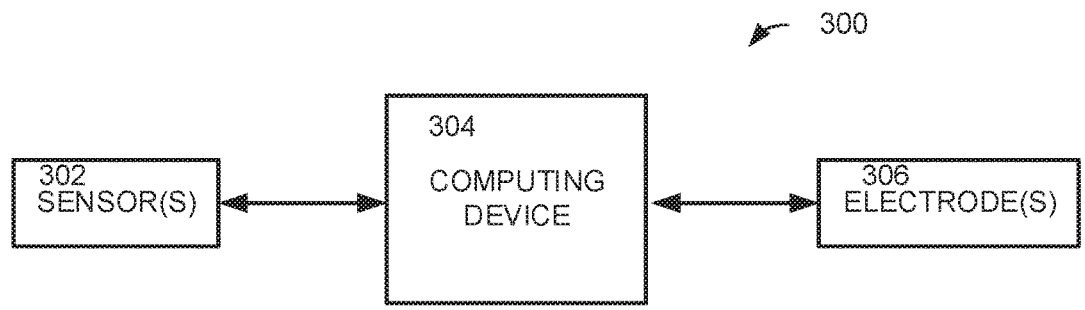
FIG. 11 is a block diagram of an example system that can provide neural stimulation according to a closed loop algorithm to treat sleep disordered breathing (SDB), which can be part of the system of FIG. 1.

With reference to FIG. 11, system 300 can be implemented within the system 10 and/or the stimulator 20 to provide stimulation to improve SDB according to open-loop control or closed-loop control. The system can include one or more sensors 302 (which can be implanted and/or external), a computing device 304 (which can be implanted and/or external, and may be part of another device like the controller), and one or more electrodes 306 (which can be implanted and/or external). The one or more sensors can be configured to record/detect physiological data (e.g. data originating from the patient's body) over time including changes therein. Exemplary physiological data can include phasic contraction of anterior lingual musculature, such as phasic genioglossus muscle contraction, underlying tonic activity of anterior lingual musculature, such as tonic activity of the genioglossus muscle, and combinations thereof. Phasic contraction of the genioglossus muscle can be indicative of inspiration, particularly the phasic activity that is layered within the underlying tonic tone of the genioglossus muscle. Changes in physiological data include changes in phasic contraction of anterior lingual musculature, such as phasic genioglossus muscle contraction, changes in underlying tonic activity of anterior lingual musculature, such as changes in tonic activity of the genioglossus muscle, and combinations thereof. For example, EMG signal changes can include changes in the frequency, amplitude, spike rate, or other features within the EMG signal. In particular, changes in phasic contraction of the genioglossus muscle can indicate a respiration or inspiration change and can be used to as a trigger for stimulation. Such physiological data and changes therein can be identified in recorded EMG signals, such as during different phases of respiration including inspiration. As such, one or more sensors 302 can include EMG sensors. The one or more sensors 302 can also include, for example, wireless or tethered sensors that measure, body temperature, movement, breath sounds (e.g. audio sensors), heart rate, pulse oximetry, eye motion, etc.

The computing device 304 can be configured to provide open-loop control and/or closed-loop stimulation to configure parameters for a stimulation. In other words, with respect to closed-loop stimulation, the computing device can be configured to track the patient's respiration (such as each breath of the patient) and stimulation can be applied during inspiration, for example. However, with respect to open-loop stimulation, stimulation can be applying without tracking specific physiological data, such as respiration or inspiration. However, even under such an "open loop" scenario, the computing device can still adjust stimulation and record data, to act on such information. For example, one way the computing device can act upon such information is that the computing device can configure parameters for stimulation to apply stimulation in an open loop fashion but can monitor the patient's respiration to know when to revert to applying stimulation on a breath to breath, close-loop fashion such that the system is always working in a close looped algorithm to assess data. Accordingly, adjustments to stimulation may be based on an input to the computing device 304, which may be based on one or more trends in physiological data recorded by the one or more sensors 302 over time. Treatment parameters of the system may be automatically adjusted in response to the physiological data. The physiological data can be stored over time and examined to change the treatment parameters; for example, the treatment data can be examined in real time to make a real time change to the treatment parameters.

The one or more electrodes 306 can deliver the stimulation configured according to the parameters. In some instances, the sensing component 302 and the electrode 306 can be the same structure or element. Advantageously, use of a single structure or element as the sensing component 302 and the electrode 306 reduces the invasive nature of the surgical procedure associated with implanting the system, while also reducing the number of foreign bodies introduced into a subject. In certain aspects, the sensing component and the electrode are disposed on the same device, such as a neuromodulation lead.

Figure 12:
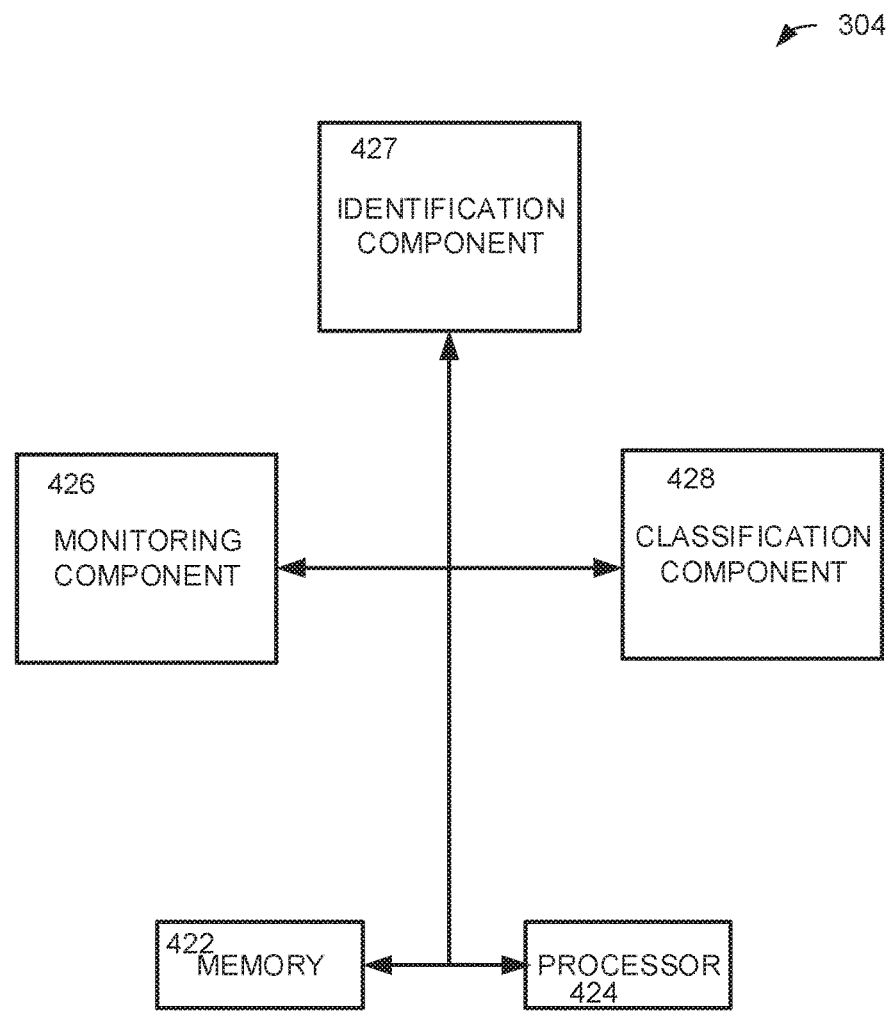
FIG. 12 is a block diagram of an example of the computing device shown in FIG. 11.

An example of the computing device 304 programmed to implement the closed-loop scenario is shown in FIG. 12. The computing device 304 can include a memory 422 (e.g., a non-transitory memory), a processor 424 (e.g., an integrated circuit, such as an application specific integrated circuit (ASIC)), or an ASIC comprising both a memory and a processor. For example, the memory 422 can be a computer-usable or computer-readable medium that can contain or store the machine-readable instructions (which are, for example, a program) for use by or in connection with the instruction or execution of a system, apparatus or device (like the computing device 304) by the processor 424. The computer-usable or computer-readable medium can be, for example but not limited to, random access memory (RAM) including static or dynamic RAM, read-only memory (ROM), flash memory, an Erasable Programmable Read Only Memory (EPROM), floating point memory, or combination thereof including combinations thereof on the same ASIC. The processor 424, for example, can include one or more processing cores, processing units, or the like. The memory 422 can store machine readable instructions, while the processor 424 can access the memory 422 and execute the machine readable instructions (e.g., which can include one or more programs) and cause the computing device 304 to perform operations of a monitoring component 426, an identification component 427, and/or a classification component 428. The processor 424 can interpret the physiological information coming from the sensors, including decoding data, analyzing data, recognizing patterns, etc.

The monitoring component 426 can monitor the physiological data recorded by the sensor(s) 302. The identification component 427 can identify a trigger within the physiological data (e.g., related to respiration). For example, the monitoring component can monitor EMG waveform characteristics like spike rate, amplitude, and frequency, as well as phasic activity and tonic activity (again monitoring for changes in amplitude, frequency or other parameters of the EMG). The identification component can identify the trigger during such monitoring (e.g. a characteristic change in the EMG waveform). In one example, the trigger can be an associated change in the EMG, such as short term contraction of the genioglossus muscle indicating phasic genioglossus muscle activity or longer term changes in genioglossus muscle activity indicating a change in underlying tonic tone of the genioglossus muscle seen over one or more parts or repetitions of the physiological data. The trigger can be identified as a biomarker for a condition related to sleep, such as a change in at least one parameter physiological data. In some instances, the biomarker can be inspiration. In other instances, the biomarker can be a body position. In other instances, the biomarker can be a stage in a sleep cycle (e.g., awake, non-REM sleep—stage 1 light sleep, stage 2 light sleep, stage 3 deep sleep, REM sleep, etc.). In some instances, motion detection and/or other biomarkers can be used to automatically turn the therapy on only once the patient has fallen asleep and to determine the parameters of stimulation to optimally maintain airway patency throughout the night (including adapting stimulation based on sleep stage and body position) without causing unnecessary discomfort or leading to arousal events to increase patient comfort and adherence to therapy. Stimulation can be ramped up as the patient moves from light to deep sleep or ramped during each stimulation phase such that the first pulse in a pulse train has less amplitude and/or pulse width than the last pulse in the pulse train. In some instances, stimulation will automatically shut off if the patient wakes up and re-initiate as they fall back to sleep.

The awake stage of the sleep cycle refers to a relaxation stage when the subject is first lying in bed or lying in bed trying to fall asleep again. Non-REM sleep has three stages and is a stage of sleep without rapid eye movement. The REM stage includes REM sleep, where eyes move rapidly from side to side behind closed eyelids, breathing becomes faster and irregular, heart rate and blood pressure increase to near waking levels, and arm and leg muscles become temporarily paralyzed.

Non-REM stage 1 refers to the changeover from wakefulness to sleep (lasting several minutes). During non-REM stage 1, a subject's heartbeat, breathing, and eye movements slow and muscles relax with occasional twitches. Non-REM stage 2, the longest of all the stages, is a period of light sleep before entering deeper sleep, where heartbeat and breathing slow, muscles relax even further, body temperature drops and eye movement stops. Non-REM stage 3 refers to the period of deep sleep needed to feel refreshed in the morning, where heartbeat and breathing slow to their lowest levels during sleep, muscles are relaxed, and it may be difficult to awaken.

The sleep state can be determined, for example, based on information in the physiological data (e.g., tonic genioglossus muscle activity as indicated on an EMG). Once the sleep state is recognized, the goal is to apply therapy in such a way to minimize patient discomfort and to also minimize potential stimulation related arousal events. This may include, reducing the amplitude of stimulation during stage 1 and stage 2 sleep, and increase amplitude during stage 3 and REM. This may also include ramping therapy over a longer period of time, meaning from zero to programmed output over a longer time period, during stage 1 and 2 sleep vs. stage 3 and REM sleep or ramping therapy within each pulse train, when applied during inspiration for example.

For example, if certain EMG activity is detected, like phasic changes in EMG activity that is indicative of inspiration during any phase of sleep, the system may deliver stimulation during the respiratory period of inspiration. The system can apply stimulation to the hypoglossal nerve, for example, using a particular set of electrodes, waveform, pulse width, frequency, intra-pulse interval and pulse ramp rate that provide therapeutic airway patency during inspiration. The system can stop stimulation during the exhalation period and can continue to monitor the physiological EMG, from the genioglossus muscle for example, throughout the inspiratory and exhalation periods of each breath. The system can adjust the stimulation parameters and/or the electrodes selected for stimulation as necessary to optimize the stimulation to provide the optimal airway patency, based on additional biomarkers including, sleep state, body position, or the like. The closed loop algorithms embedded within the stimulator or neuromodulation lead can continuously monitor and adjust therapy based on the physiological data and triggers and use rule based classification to determine when, how and for what period of time, to apply and adjust stimulation to provide optimal airway patency during sleep.

For example, if certain EMG activity, like tonic and phasic EMG activity drops or ceases during REM, the system may deliver a stimulation periodically based on predetermined physician programmed parameters, the system may rely on previous known patient specific parameters to apply stimulation, or the system may use a default periodic stimulation that is applied throughout REM sleep. The system can also monitor EMG through the REM period to determine when to stop using the periodic stimulation and when to re-initiate applying stimulation during each inspiratory event.

In some instances, the system may not turn on stimulation immediately when the stimulator is within the field from the transmit coil. In this case, the system can turn on and monitor an EMG signal, e.g., detecting tonic and phasic muscle activity, to understand the sleep stage. Once the system has determined the patient is sleeping, entering stage 1 of sleep or stage 2 of sleep, the system 10 can start to provide therapy in a physiological manner, e.g., starting to apply small amount of stimulation using a stimulus ramp during each stimulation period, such that unnecessary arousal events or discomfort is not caused during initial phases of sleep. In this configuration, the EMG may be monitored for several minutes or several hours to determine the state before the system initiates therapy. Many individuals with OSA also suffer from insomnia, in which the individual has trouble falling asleep, and in this case, a negative feedback loop can cause the patient additional anxiety, such that they are fearful that the therapy will turn on prior to when they fall asleep and as such are not relaxed enough to fall asleep. This can cause the individual to turn off therapy, or over time discontinue use of the therapy. A "smart" system that is able to recognize when patients are asleep and apply therapy such that it is physiological will increase therapy adherence and efficacy. Once the system recognizes non-REM stage 1, for example, the system can start to recognize non-REM stage 2, non-REM stage 3, REM sleep, or the like.

For example, the ASIC (an example of processor 424) can be configured to control a custom algorithm, which can control the therapy application. For example, the ASIC can be configured to run embedded digital logic that uses information gathered by an EMG sensor to decide when, for how long, and at what stimulation parameters to stimulate to provide the optimal therapy to the subject to control the volume of air capable of flowing through the upper airway, also known as airway patency. The embedded digital logic can sense EMG activity, which can be known to the algorithm to correspond with respiration, more specifically to inspiration and exhalation. The algorithm can decode the EMG activity to trigger stimulation of the anterior musculature and/or the hypoglossal nerve (including distal branches thereof) bilaterally, for example, to open the airway, such that the therapy is linked to each respiration, each inspiration and each exhalation, for example. Therapy can thus be provided during each breath, specifically during inspiration, for example, all by using embedded correlative knowledge of the EMG features that correspond to respiration. The embedded logic can include knowledge of EMG features that are specific to body position, chin position, sleep state (e.g. REM, non-REM), movement, and other physiological parameters that can elucidate and optimize therapy. The algorithm can use adaptive learning to learn individual subject specific EMG features that correlate to the above physiological states during sleep to provide additional optimization that is subject specific. The adaptive learning can be done manually with physician input or may be done completely within the algorithm based on pre-determined limits and knowledge or can be done with the cloud database and the additional adaptive learning that the cloud software can use to analyze the data from each patient and each sleep session. The algorithm, while still based on respiratory information sensed through the EMG sensor, can also have different modes. In one mode, the algorithm can be running and can provide therapy breath to breath, specifically during inspiration; in another mode, the algorithm can be learning, looking for inputs from the EMG and also from the user (e.g. patient, physician, etc.); in another mode, the algorithm can provide more continuous control of the airway, providing periodic stimulation that can be sustained for periods of time. In another mode, the algorithm can be sensing EMG information, but not providing therapy breath to breath, instead waiting until a forthcoming collapse of the airway has been identified and reacting by providing therapy that prevents the collapse from occurring. The EMG information can include, the amplitude of the EMG, the frequency components of the EMG, spike sensing, envelope sensing, and other features that can be taken directly from the EMG signal to control the algorithm and provide biomarkers for respiration and for collapse of the airway. It is understood, that the algorithm may use any or all of these features throughout the sleep period and can switch between modes based on the EMG activity as sensed by the EMG sensor or the system may be hard programmed to only run one algorithm.

The system can apply therapy in a manner that is not causing discomfort and/or arousal events in the patient. As the patient moves through the stages over the course of the entire night, the system can continuously adapt to the sleep stage (and/or patient need). For example, the largest need for stimulation can be during deep sleep (non-REM stage 3) and REM, where discomfort and arousal are unlikely, so the system can apply more stimulation, since arousal and discomfort are unlikely during these stages. The amount of time the patient is spending in each stage of sleep can also be tracked, which is very useful for tracking outcomes, as most OSA patient do not enter into deep sleep often due to arousals.

The classification component 428 can apply a rule-based classification to the trigger to determine whether one or more stimulation parameters applied by one or more of the stimulating electrodes should be altered based on a biomarker related to sleep. As stated above, biomarkers include respiration phase (such as inspiration including periods within inspiration), sleep stage during one or more sleep cycles, and/or body position during sleep as indicated by an EMG or other sensor or sensed activity. Stimulation parameters, as stated above, include, for example, pulse width, amplitude, frequency, waveform shape, electrode position/configuration, or the like). Initial rules of the rule-based classification used by the algorithm can be set for the patient and/or set based on historical values for a population, historical values for a patient, and/or patient derived values. Subsequent rules of the algorithm can be learned and/or updated and/or personalized based on an artificial intelligence learning process.

Feedback related to the stimulation (e.g., after it is delivered) can be given to the computing device 304. The computing device 304 can receive the feedback and may change one or more stimulation parameters.

An example closed-loop control scenario involves the one or more sensors 302 (implanted adjacent to an anterior lingual muscle, such as the genioglossus muscle) that can detect/record physiological data over time. The physiological data can include EMG data from the musculature of the anterior airway, which can include characteristic signals that correlate to respiration, but also can correlate to sleep position, sleep state, and/or other physiological characteristics important for the treatment of SDB. The computing device 304 can monitor the physiological data recorded by the one or more sensors 302 to identify a trigger within the physiological data. The trigger can be identified as a biomarker for a condition related to sleep (e.g., inspiration). A rule-based classification can be applied to the trigger to determine whether one or more parameters of the stimulation (e.g., delivered by one or more electrodes 306 or electrode contacts to the hypoglossal nerves) should be altered based on the biomarker.

Changes in voltages on the transmit receptor can be sensed, as well as on the power receiver and resulting changes in impedances to determine the position and movement of the power receptor within the magnetic field. In this aspect, the changes in voltage and impedance between the two coils of the power antenna can provide additional information to the system to inform the close loop algorithm and to inform additional refinement to the therapy. This type of position sensor may have additional usages beyond therapy optimization as it may provide additional data about sleep quality over time, as well as health related information. In addition, the impedance data between the coils can be correlated with activity, which can be used to also track wake vs. sleep cycles. These data along with EMG data, e.g. tonic EMG activity from the genioglossus muscle, can be used together to understand and learn wake vs. sleep throughout the period spent attempting to sleep (e.g., when the power receive coil is within the inductive field volume of the transmit coil).

Several wired or wireless input applications, including smart phone or tablet applications can also be used, wireless remote controls for example. These additional input applications can provide additional inputs to the system to adjust the therapy, adjust the closed loop algorithm, adjust stimulation outputs, adjust optimization or to adjust the algorithm mode as necessary. The input application can display electromyogram data for the user, allows the user to adjust the parameters that control the EMG collection, such as the input filters, trigger amplitudes, frequency ranges, etc.

An input application can also allow for automated therapy titration. In this mode, the application can run custom software that provides stimulation to a target site of the subject, such as a target nerve or target muscle and monitors the resulting evoked EMG activity of a muscle, such as an anterior lingual muscle, including the genioglossus muscle. The resulting EMG activity can correlate to the amount of airway opening desired (as inputted into the application) and thus can allow for automated therapeutic stimulation parameter settings and eliminate time consuming parameter adjustments during sleep Non-limiting example of stimulation parameter settings include stimulation pulse width, amplitude, frequency, electrode position/configuration and the like. In this aspect, the system can determine the therapeutic stimulation outputs and allows the subject/physician to fine tune as necessary. The subject or physician can rerun the automated parameter adjustment application at any time, and through the applications can be monitored remotely so that titration, programming can be done from the comfort of the subject's home.

The resultant evoked EMG signal can be continuously monitored and stimulation parameters needed to produce the required tongue motion for effective treatment can be determined, even if the response to a given set of stimulation parameters changes over time, effectively reducing the amount of testing required for initial programming as well as the need for ongoing follow-up testing. Also, issues with the therapy (e.g., stimulation according to certain stimulation parameter settings is not providing the tongue movement necessary to open the airway) can be identified and alerts can be generated for the patient and/or physician (this allows for quicker response and proactive management of the system).

Figure 13:
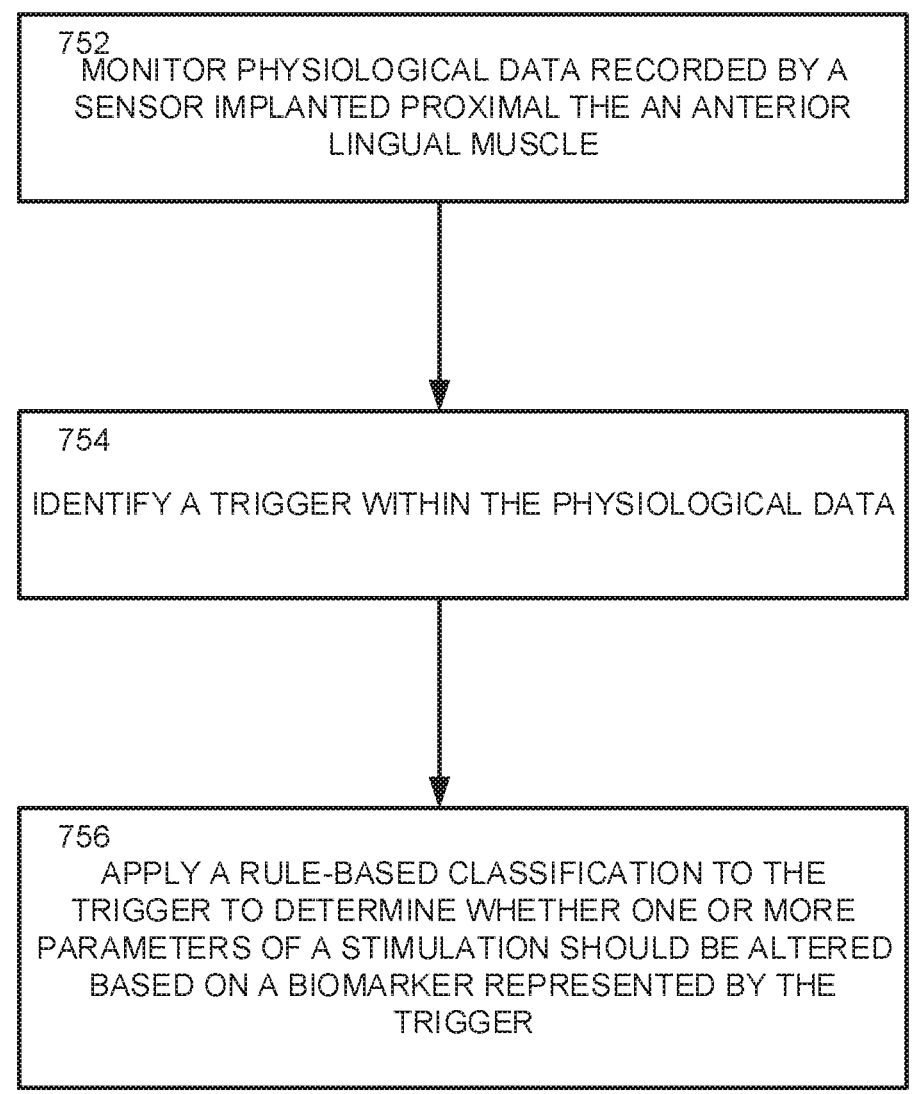
FIG. 13 is a process flow diagram of an example method for providing neural stimulation according to a closed loop algorithm to treat SDB, including OSA.

Another aspect of the present disclosure can include a method 700 (FIG. 13) for providing neural and/or muscular stimulation according to a closed loop algorithm to treat SDB. The method 700 can be executed by components of the systems as described and shown in the figures, for example. Portions of the method 700 can be stored at least in part on a non-transitory memory and executed by a processor.

For purposes of simplicity, the method 700 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 700 and/or more than the illustrated aspects may be required to implement the method 700. Additionally, one or more aspects of the method 700 can be stored in one or more non-transitory memory devices and executed by one or more hardware processors.

At 752, physiological data (e.g., related to inspiration, sleep stage and/or body position as indicated by an EMG, for example) recorded by one or more sensors can be monitored. The one or more sensors can be implanted adjacent to the anterior lingual muscle, such as the genioglossus muscle, or in the plane between the genioglossus muscle and geniohyoid muscle, for example. At 754, a trigger can be identified within the physiological data. The trigger be a change in at least one parameter of the physiological data (e.g., indicative of inspiration during respiration, body position, and/or a stage in the sleep cycle as indicated by an EMG, for example).

At 756, a rule-based classification can be applied to the trigger to determine whether one or more parameters of the stimulation should be altered based on a biomarker represented by the trigger. A signal comprising configuration/setting information for the parameters can be sent to one or more electrodes located adjacent to the hypoglossal nerve, for example. The stimulation parameter(s) can be titrated and adapted based on the trigger to optimize airway muscle tone.

Stimulator Configuration

Figure 2:
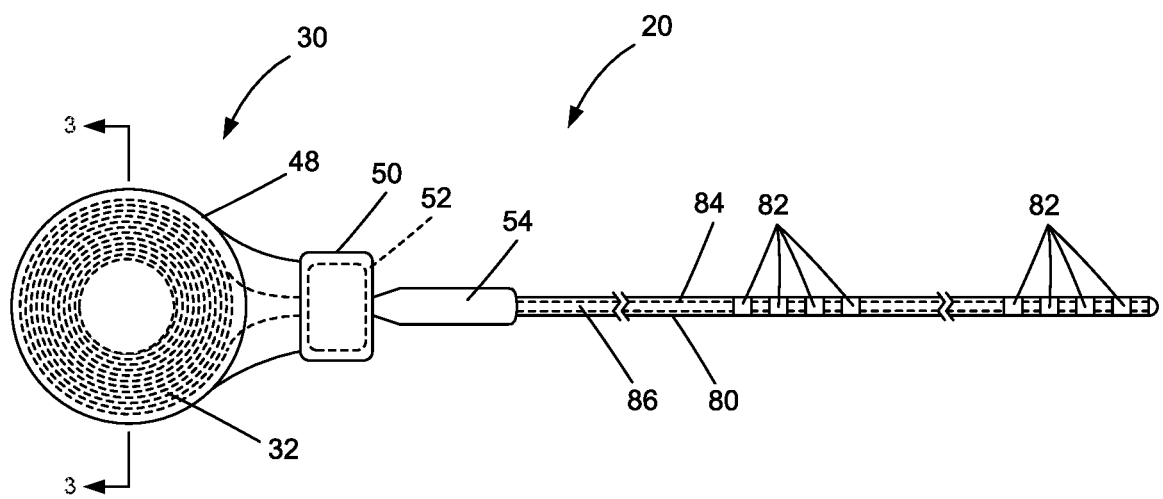
FIG. 2 is a schematic illustration of an implantable stimulator portion of an implantable stimulation system according to an aspect of the present disclosure.

The stimulator can have a variety of configurations, which can be tailored to the specific therapy being applied and/or to the anatomy at the site at which the stimulation therapy is applied. An example configuration of the stimulator 20 is illustrated in FIG. 2. Stimulator 20 can include power receiver 30, electronics package 50, and stimulator lead 80. Power receiver 30 can include a coiled receiver antenna 32 that is packaged in a protective biocompatible material and is operatively connected to the electronics package 50 and electronic components 52 mounted therein.

The stimulator lead 80 is also operatively connected to the electronics package 50, which controls the operation of the electrodes 82. In the example configuration of the present disclosure, stimulator 20 includes pigtail connector 54, which extends from electronics package 50 and can facilitate connecting stimulator lead 80 to the electronics package. Pigtail connector 54 can facilitate a detachable connection between electronics package 50 and stimulator lead 80 so that leads of different configurations can be connected to the electronics package. This can facilitate manufacturing of the stimulator lead 80. This can also allow a physician to select a lead having a desired size and/or configuration.

Additionally, the stimulator lead 80 being separate from, and connectable to, the remainder of the stimulator 20 via the pigtail connector 54, can facilitate implanting the lead separately. As a result, implanting the lead 80 can be much less invasive, allowing the lead to be placed via a small incision. An integrated design could necessitate a larger incision and also the need to handle and manipulate the entire stimulator 20 as a whole during the implantation process, which could complicate the lead placement, as the surgeon could have to work around the remainder of the stimulator 20, e.g., the electronics package 50 and the antenna 32.

Stimulator lead 80 can be generally elongated and includes a plurality of electrodes 82 spaced along its length. Electrodes 82 can be electrically connected to electronics package 50 by conductors, such as wires, that are illustrated schematically at 84 by dashed lines in FIG. 2. In the example configuration illustrated in FIG. 2, stimulator 20 has an eight-channel, eight electrode configuration, meaning that stimulator lead 80 includes eight electrodes 82, each having its own dedicated channel. Stimulator 20 can be configured to have a greater number of channels or fewer channels. Additionally or alternatively, stimulator 20 can include more than one lead, again depending on the specific therapy and/or the targeted anatomical structure. Regardless of the number of leads or channels, each electrode 82 can be configured and utilized independently of the other electrodes. Because of this, all or some of electrodes 82, whichever is determined to be most effective for a particular implementation, can be utilized during the application of stimulation therapy.

Electrodes 82 can be utilized as stimulating electrodes or sensing electrodes. Stimulating electrodes can used to apply stimulation to a target anatomical structure, such as, for example, a nerve or muscle. Sensing electrodes can be used to detect and measure an EMG response, for example, from a neuromuscular structure associated with the target nerve. For a SDB treatment implementation illustrated in this description, the target nerve can be the HGN and the associated muscle can be the genioglossus muscle. The stimulator can, however, be used to target other nerves and to measure physiological electrical signals from other anatomical structures, such as EMG responses, from other neuromuscular structures.

In the example configuration of FIG. 2, electrodes 82 are arranged in two groups of four electrodes spaced along the length of lead 80. One group of electrodes 82 can be positioned distally near an end of lead 80 and one group can be positioned proximally, between the distal group and electronics package 50. The configuration of electrodes 82 can, however, vary. The stimulator can include a different number of electrodes (two or more), and/or the electrodes can be grouped, spaced, or otherwise arranged in different configurations along the length of the lead. As mentioned previously, the stimulator can also include any suitable number of leads (one or more).

The identities of electrodes 82 as being stimulation electrodes or sensing electrodes can be determined by the manner in which they are controlled via electronics package 50. In certain implementations, the identities of electrodes 82 can be fixed. In a fixed implementation, certain ones of electrodes 82 can be assigned and used exclusively as stimulating electrodes and others can be assigned and used exclusively as sensing electrodes. In other implementations, the identities of electrodes 82 can be dynamic. In a dynamic implementation, electrodes 82 can be assigned and used as both stimulating and sensing electrodes. In further implementations, electrodes 82 can be implemented in combinations of fixed and variable identities.

How the electrodes are utilized depends at least in part on how the stimulator itself is implemented. In certain implementations of the stimulator, some or all of the electrodes can be positioned relative to structures, such as nerves and/or muscles for which both the application of stimulation energy and the sensing of an EMG response or other physiological electrical signal is desired. In these cases, some or all of the electrodes can be utilized as stimulating electrodes when stimulation at its location is desired, and as sensing electrodes when sensing at its location is desired. In other implementations of the stimulator, some electrodes can be positioned relative to structures for which only the application of stimulation energy is desired, and other electrodes might be positioned relative to structures for which only the sensing of EMG responses or other physiological signals is desired.

Advantageously, the identities of electrodes 82 is configured in software settings and requires no hardware configurations. The selectable configurations of electrodes 82 can be facilitated by electronic components 52 enclosed in electronics package 50. Electronic components 52 are preferably implemented in an application-specific integrated circuit (ASIC). The electronic components 52 can, however, include one or more ASICs, discrete electronic components, and electrical connectors for connecting the electronic components to power receiver 30 and/or electrode lead 80. The electronic components, whether embodied in a single ASIC or one or more components, can, for example, include processing and memory components, e.g., microcomputers or computers-on-a-chip, charge storage devices (e.g., capacitors) for accumulating a charge and supplying stimulation power, and solid state switching devices for selecting the identities of the electrodes (e.g., anode, cathode, recording electrode) and modulating power supplied to the electrodes (e.g., pulse-width modulation (PWM) switches).

To provide comfort to the patient and ease of insertion for physicians, the stimulator 20 can have a generally soft/flexible construction. This soft/flexible construction can apply to lead 80, power receiver 30, or both the lead and the power receiver. In one example configuration, the stimulator components—power receiver 30, electronics package 50, and lead 80—can be coated or otherwise encased simultaneously in a single operation, such as an insert molding with a biocompatible material, such as silicone, epoxy, and various suitable polymers.

Figure 4:
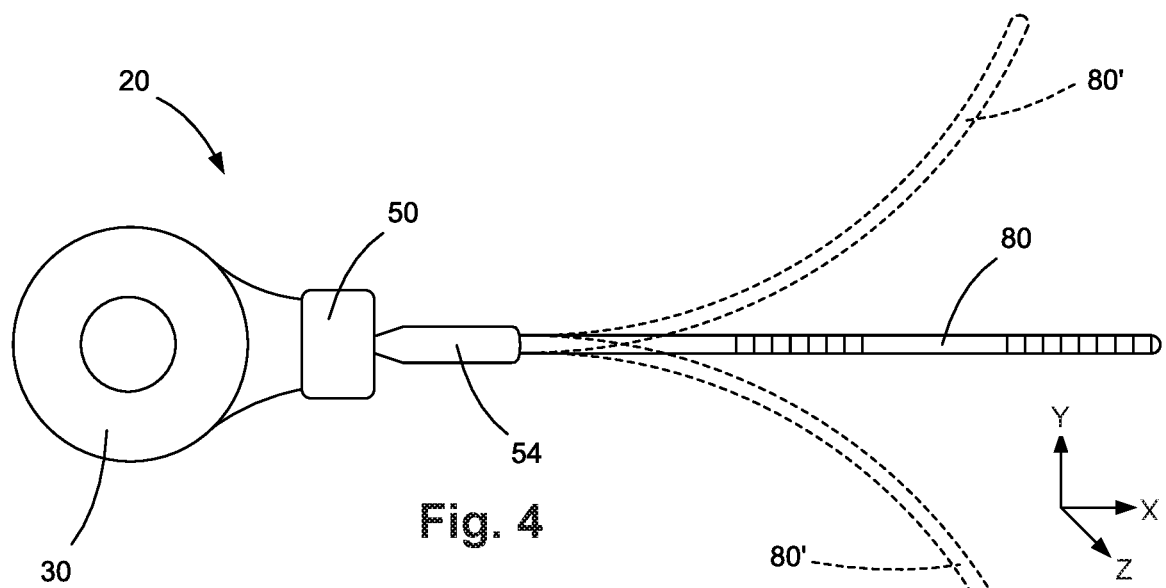
FIGS. 4-6 are schematic illustrations depicting flexible properties of an implantable stimulator according to an aspect of the present disclosure.
Figure 5:
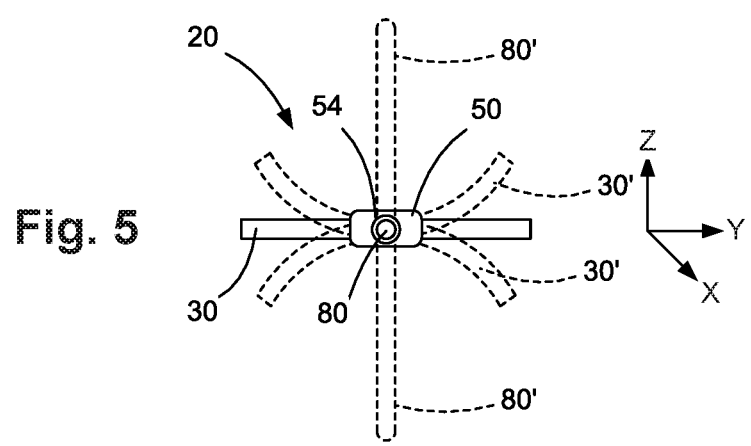
Figure 6:
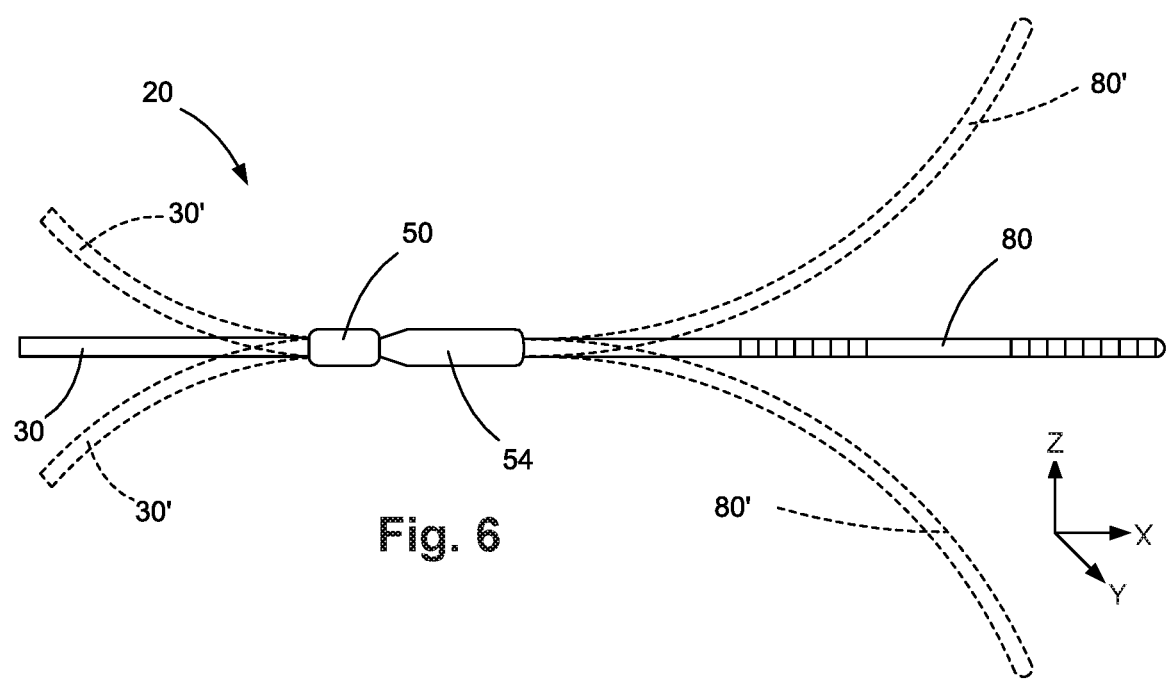

Referring to FIGS. 4-6, power receiver 30 and lead 80 can have a flexible configuration that allows either or both structures to bend or flex, which facilitates implantation compatibility with a variety of anatomical structures. Power receiver 30, can be generally flat and planar in configuration, and can bend in directions transverse to its plane which, as shown in FIGS. 4-6, is the X-Y plane. Power receiver 30 can thus bend in the Z-direction as shown in dashed lines at 30' in the Figures. Lead 80, can be generally elongated in configuration and can extend axially, along the X-axis as shown in FIGS. 4-6. Lead 80 can bend in multiple directions relative to that plane, i.e., in the direction of one or both of the Y-direction and Z-direction, as shown in dashed lines at 80' in the figures.

To facilitate the flexible configuration of lead 80, electrodes 82 and the conductors 84 (see FIG. 2) that connect the electrodes to the electronics package 50 can be encased and supported in a covering 86. Covering 86 can be formed of a biocompatible material, such as silicone and various suitable polymers, and can be configured to leave exposed electrodes 82 or portions thereof. Covering 86 can be formed, for example, in the aforementioned insert molded covering of the stimulator 20 structure.

To facilitate the flexible configuration of power receiver 30, antenna 32 can be formed on a soft substrate so as to be flexible and conform to the anatomy at the site of implantation. For example, power receiver 30 can have a flexible printed circuit board (PCB) construction in which antenna 32 is etched from a thin layer of conductive metal laminated on a substrate 38 (see FIG. 3) constructed of a flexible material, such as a polymer. In one particular flexible PCB construction, the substrate can be a polyimide material and the conductive metal can be copper. Other flexible PCB constructions can be implemented. Antenna 32 can be encased and supported in covering 48. Covering 48 can be formed of a biocompatible material, such as silicone, epoxy and various suitable polymers. Covering 48 can be formed, for example, in the aforementioned insert molded covering of the entire stimulator 20 structure.

The flexible PCB of power receiver 30 can extend into electronics package 50 and can be configured to mount the electronic components 52. The PCB can also be configured to interface conductors 84 of lead 80, and/or to form portions of the lead itself. In this instance, power receiver 30, electronics package 50, and lead 80 (or portions thereof) can be encased in the biocompatible material (e.g., silicone, epoxy and various suitable polymers) simultaneously.

While being flexible, the lead can also be configured to maintain a shape to which it is formed. This feature can, for example, be facilitated by conductors 84 that connect electrodes 82 to electronics package 50 or by an additional internal shape-maintaining (e.g., metal) support structure (not shown) that extends along its length. In either case, metal conductors 84 or the support structure can be selected or otherwise configured to possess physical properties, such as malleability/ductility, that allow the lead to be manipulated three dimensionally (3-D) into a desired shape or have a pre-determined bias and to maintain that shape or bias once formed. For example, the lead can be biased to have a certain shape that is created, for example, by heat shaping, material shaping or using other methods of manufacturing a biased lead.

Figure 7:
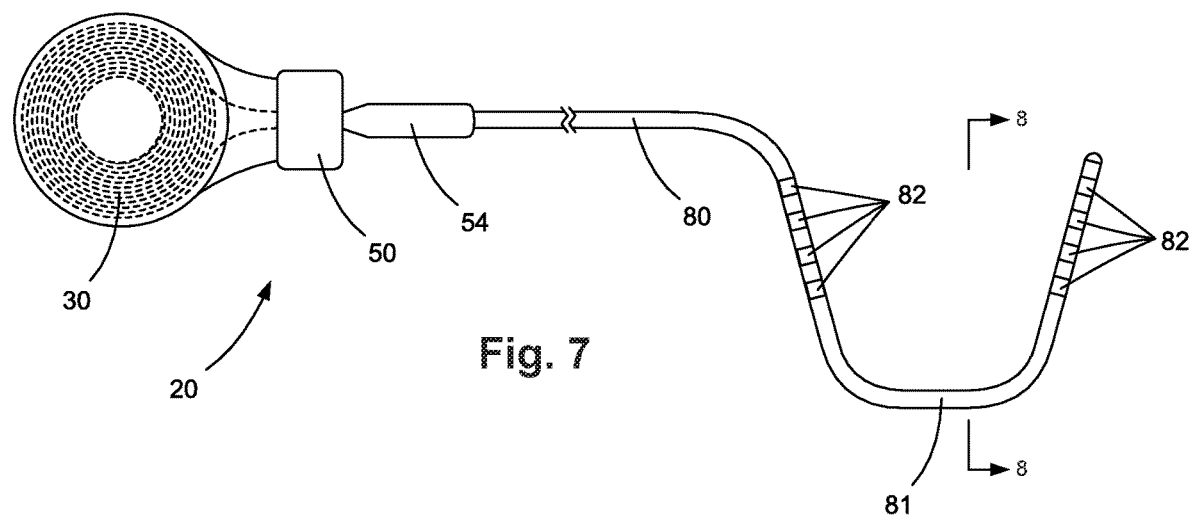
FIGS. 7-8 are schematic illustrations depicting an exemplary configuration of a lead portion of an implantable stimulator according to an aspect of the present disclosure.
Figure 8:
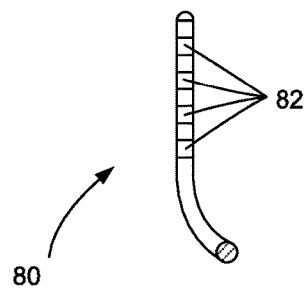

FIGS. 7-8 illustrate one such 3-D shape to which the lead 80 can be formed. The example configuration of FIGS. 7-8 shows the lead 80 formed three-dimensionally in a generally U-Shape or omega-shape, as shown in the plan view of FIG. 7, with an additional or alternative bend depth-wise as shown in FIG. 8. This particular 3-D configuration can be implemented to position the electrodes 82 at different positions along the HGN, where the stimulator is configured to treat SDB, such as OSA, for example. More specifically, the configuration of the lead 80 in FIGS. 7 and 8 can allow for the right and left electrodes 82 (as viewed in FIG. 7) to be placed in very close proximity to the HGN branches. The right and left electrodes 82 in an implanted configuration can extend along the posterior-anterior course of the HGN, placing the electrodes at or near the location of the branch points, such as distal branch points from the main trunk. This placement allows for direct electrical activation of a single branch or branches as needed for control of the posterior airway. In particular, in an aspect, a neuromodulation lead comprises a lead body having a left portion, a right portion, and an intermediate portion 81 therebetween. The neuromodulation lead further includes a plurality of electrodes comprising a left set of electrodes 82 disposed on the left portion of the lead body and a right set of electrodes 82 disposed on the right portion of the lead body. At least one of the plurality of electrodes is a stimulating electrode configured to deliver a stimulation signal to a target site. The lead body is biased towards a substantially omega shape when the neuromodulation lead is fully deployed and/or the intermediate portion 81 of the lead body is biased towards an inferior position relative to the left and right electrode sets 82 when the neuromodulation lead is fully deployed. The location of the left and right set of electrodes on the respective left and right portion of the lead body can be based on the location of a respective left and right stimulation target site comprising the hypoglossal nerve trunk, distal branches of the hypoglossal nerve, nerve branches that innervate horizontal fibers within the genioglossus muscle, nerve branches that innervate oblique fibers within the genioglossus muscle, or any suitable combination thereof when the neuromodulation lead is fully deployed.

In addition, with this implementation of lead 80, neurostimulation system 10 can be configured to stimulate bilaterally or unilaterally as needed without unnecessary or unwanted stimulation of surrounding structures. Because of the 3-D biased nature of the lead 80 and the synchronous manner in which the anterior lingual muscle move, additional anchoring structures may be unnecessary. For example, the inferior bend of the lead in intermediate portion 81 can allow for force to be exerted against the genioglossus muscle by the lead, since the genioglossus muscle has a convex shape (when viewed inferiorly) to allow for better contact between the electrode sets and the genioglossus muscle.

The power receiver is designed with the goal of delivering maximum power to the stimulator from a given external magnetic field. With this goal in mind, for the HGN stimulation implementation of the example configuration disclosed herein, power receiver 30 and receiving antenna 32 have a unique configuration designed to adhere to several criteria for stimulator 20. The criteria depend, of course, on the intended therapeutic use of the system and the configuration resulting therefrom. The criteria set forth below are specific to an example configuration of system 10 for treating SDB including OSA via neuromodulation of the HGN:

- The stimulator 20 operates within the guidelines for maximum permissible magnetic field exposure as recommended in IEEE Standard C95.1-2005 (Reference 3).
- The receiving antenna 32 allows for near continuous power consumption (10-30 milliwatts (mW)) from the stimulator 20.
- The receiving antenna operates at a frequency ranging from 100 kHz to 2.4 GHz ISM (industrial, scientific, medical band of the radiofrequency spectrum). In one particular implementation, frequencies of 6.78 MHz or 13.56 MHz were used.
- The receiving antenna 32 has a diameter of 2-3 cm. and be as thin as possible to maintain flexibility.
- The stimulator 20 is small enough for minimally invasive subcutaneous implantation within the soft tissue of the sub-maxillary neck.
- The stimulator 20 maintains a soft, flexible design so that it can be manipulated to conform to the anatomy of the patient.

Other stimulation therapies or implementations of the implantable stimulation system 10 can cause some or all of these criteria to be changed or adjusted, and also for certain criteria to be added or removed.

Figure 3:
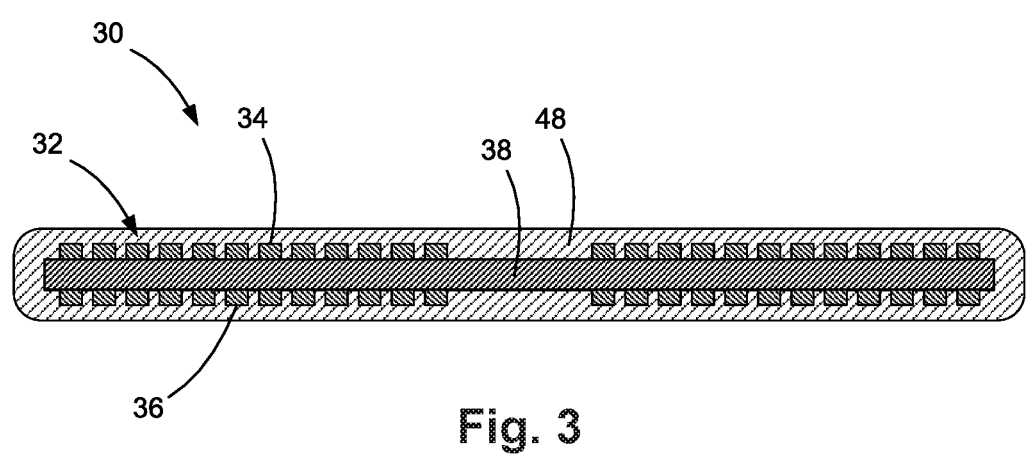
FIG. 3 is a section view taken generally along line 3-3 of FIG. 2, illustrating an antenna portion of the implantable stimulator.

To meet these criteria, receiving antenna 32 can have a double-layer, flat, "pancake" configuration. Referring to FIG. 3, antenna 32 can have a flexible PCB construction in which first or upper/top antenna coil 34 is formed on a first or upper/top side of substrate 38 and second or lower/bottom antenna coil 36 is formed on a second or lower/bottom side of the substrate. Substrate 38 can be a thin (e.g., 1 to 3 mil) polyimide layer and coils 34, 36 can be etched from thin layers of copper or gold (e.g., 1 oz./ft$^2$≈1.4 mil) laminated onto substrate 38.

PCB 38 can also support electronic components 52 in electronics package 50. Using guidelines for maximum permissible magnetic field exposure, IEEE Standard C95.1-2005 (which is incorporated herein by reference in its entirety), the maximum achievable delivered power is approximately 10-30 mW at 6.78 MHz frequency. These power requirements were chosen based on the estimated requirements for components 52 of electronics package 50, the estimated maximum stimulation parameters, and preclinical studies, while also including a safety factor to allow for capacitor charging and to provide transitional power. Transitional power can be provided via a variety of components, such as capacitors, supercapacitors, ultracapacitors, or even a rechargeable power source, such as a battery. Continuous power during patient movement, especially at the high end of power ratios and/or when coupling is not ideal. The transitional power source helps ensure complete, continuous operation of the stimulator 20, even during patient movement.

Those skilled in the art will appreciate that, in operation, an antenna can be susceptible to power losses due to substrate losses and parasitic capacitance between coils 34, 36 and between the individual coil turns. Substrate losses occur due to eddy currents in the substrate due to the non-zero resistance of the substrate material. Parasitic capacitance occurs when these adjacent components are at different voltages, creating an electric field that results in a stored charge. All circuit elements possess this internal capacitance, which can cause their behavior to depart from that of "ideal" circuit elements.

Advantageously, antenna 32 can implement a unique two-layer, pancake style coil configuration in which coils 34, 36 are configured in parallel. As a result, coils 34, 36 can generate an equal or substantially equal induced voltage potential when subjected to an electromagnetic field. This can help to equalize the voltage of coils 34, 36 during use, and has been shown to significantly reduce the parasitic capacitance of antenna 32. In this parallel coil configuration of antenna 32, top and bottom coils 34, 36 are shorted together within each turn. This design has been found to retain the benefit of lower series resistance in a two-layer design while, at the same time, greatly reducing the parasitic capacitance and producing a high maximum power output.

Figure 9A:
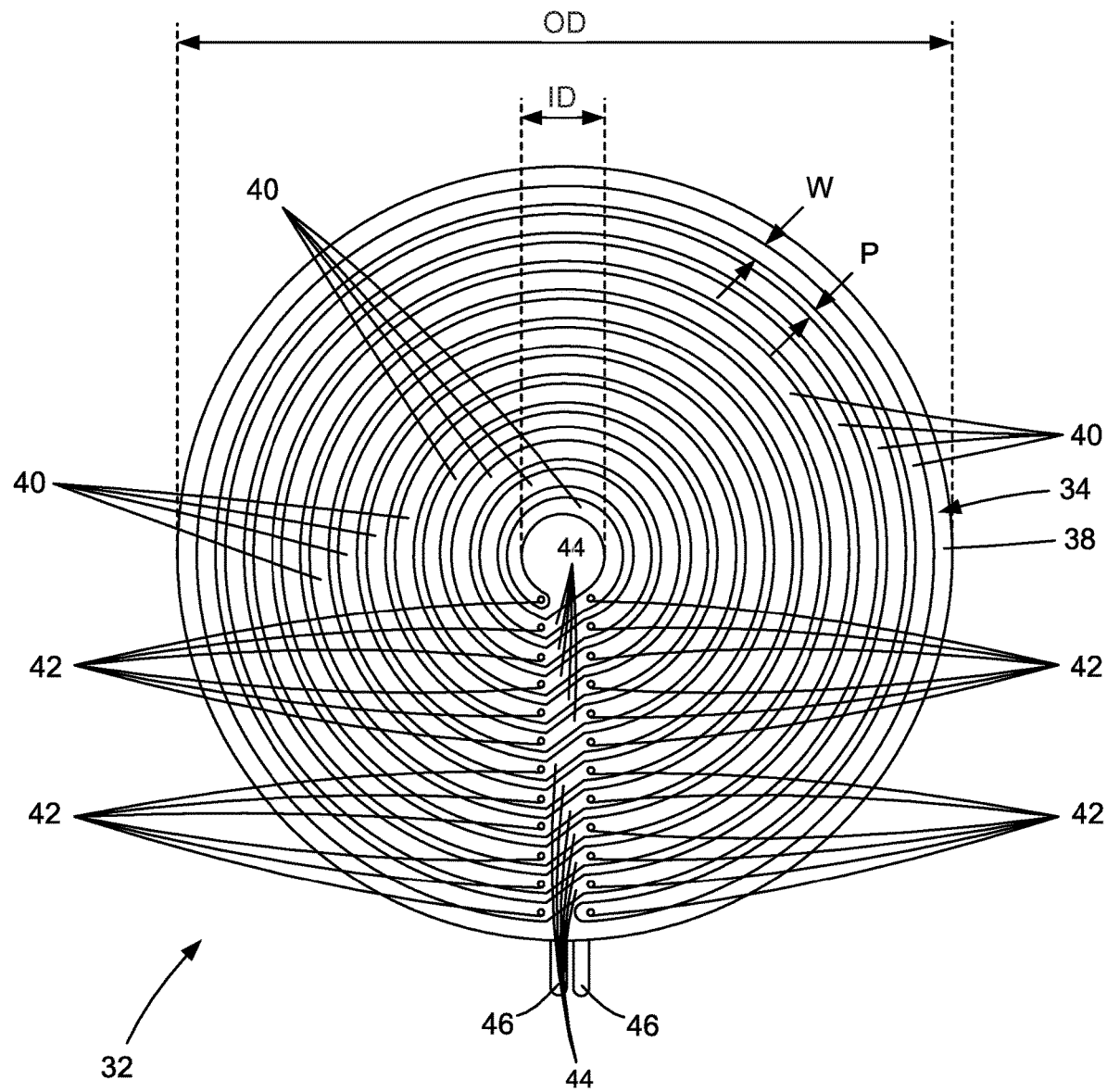
FIGS. 9A-9B are schematic illustrations depicting an exemplary configuration of an antenna portion of an implantable stimulator according to an aspect of the present disclosure.
Figure 9B:
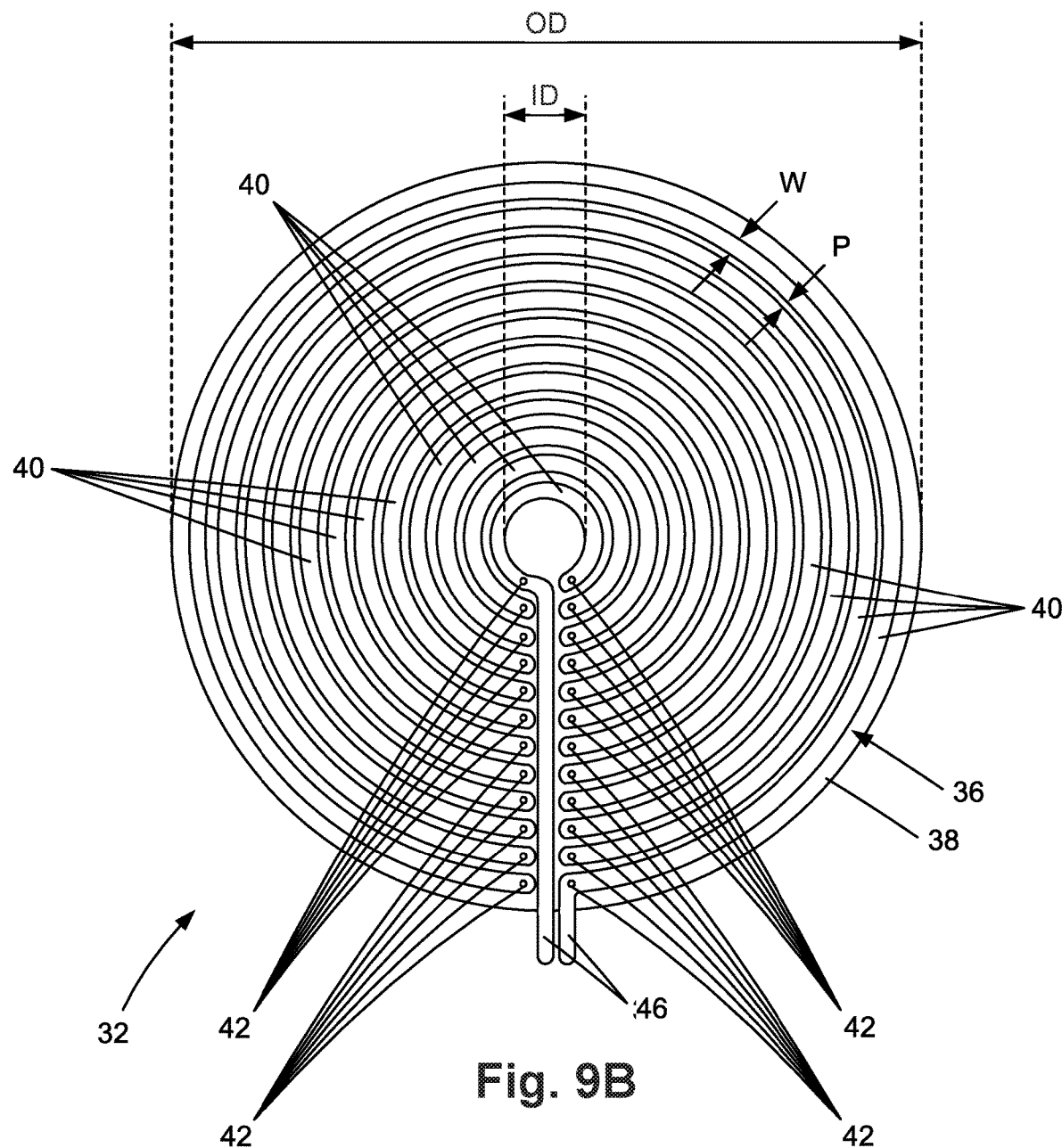

This improved, parallel configuration of antenna 32 is illustrated in FIGS. 9A and 9B, which illustrate the top and bottom coils 34 and 36, respectively, on PCB substrate 38. Each coil 34, 36 can include a plurality of coil windings or turns 40 and can be characterized by the following properties: number of turns (N), outside diameter (OD), coil pitch (P), trace width (W), trace thickness (T), and coil spacing (S). These properties are measured as follows:

- The OD is the diameter of coil 34, 36 measured across the coil between outer edges of outermost turn 40.
- The coil pitch P is the spacing between turns 40 measured between any two adjacent turns.
- The coil width W is the width of each coil turn 40.
- The trace thickness T is the thickness of turns 40, which is determined by the thickness of the conductive (Cu) layers laminated onto substrate 38 in the PCB construction.
- The coil spacing S is the distance between coils 34, 36, which is determined by the thickness of substrate 38 in the PCB construction.

In one particular configuration of antenna 32, PCB substrate 38 is a 2 mil polyimide layer and coils 34, 36 are etched from 1.4 mil copper laminated onto the substrate. The parallel coil configuration of the antenna 32 results from electrically connecting the turns 40 of the coils 34, 36 through substrate 38. These connections can be in the form of electrically conductive connectors illustrated at 42 in FIGS. 9A and 9B. Connectors 42 between the turns 40 can, for example, be formed by drilling or laser etching holes through the PCB structure, e.g., through substrate 38 and turns 40 of the upper and lower coils 34, 36, and plating or filling the holes with a metal, such as plated copper/gold or melted and/or flowed tin-lead, for example, to electrically connect the turns on the opposite surfaces of the substrate. The connectors could also be formed mechanically, e.g., pins or rivets.

Coils 34, 36 of antenna 32 have a unique configuration that allows for their parallel interconnection. On each side of antenna 32, turns 40 are semi-circular, each having a fixed diameter with closely spaced ends. This is opposed to a traditional coil configuration in which the diameter of the turns varies continuously in a spiral that decreases progressively from outside to inside. To create the coiled configuration of the antenna 32, on one side of the antenna (upper coil 34 side in the example configuration of FIG. 9A), links 44 can extend diagonally between adjacent turns 40 of upper coil 34. Links 44 can be formed as portions of the copper layer, for example, laminated onto substrate 38, and therefore can be formed coextensively with turns 40 of upper coil 34 as one continuous conductive (Cu) strip. Upper coil 34 can therefore be configured as a continuous coil having decreasing diameter from outside to inside and can therefore function as a spirally configured coil.

On the lower coil 36 side of antenna 32, turns 40 can also be semi-circular, each having a fixed diameter with closely spaced ends. There can be no links connecting adjacent turns 40 of lower coil 36. Instead, on the lower coil 36 side of antenna 32, terminals 46 can be formed—one connected to a terminal end of the innermost turn of the lower coil, and one connected to a terminal end of the outermost turn of the lower coil. Terminals 46 can be connected to innermost turn 40 and can extend in the space between the ends of the remaining turns.

Viewing FIGS. 9A and 9B, turns 40 of upper and lower coils 34, 36 can be interconnected at each of connectors 42. Through connectors 42, the links 44 interconnecting the adjacent turns 40 of the upper coil 34 can also interconnect the adjacent turns of lower coil 36. Thus, turns 40 of the lower coil 36 also can be arranged in a continuous coiled configuration through connectors 42 and links 44. Lower coil 36 therefore can be configured as a continuous coil having decreasing diameter from outside to inside and can therefore function as a spirally configured coil.

Terminals 46 can be electrically connected to both upper coil 34 and lower coil 36 through connectors 42. The terminal ends from which terminals 46 extend can be radially opposite ends of inner and outer turns 40. As shown, terminal 46 of innermost turn 40 is connected to a first end of the turn, on a first side of the space between the opposite ends of the turns; whereas the terminal of outermost turn 40 is connected to an opposite second end of the turn, on an opposite second side of the space between the opposite ends of the turns.

For the configuration illustrated in FIGS. 9A and 9B, the performance of the antenna can depend on the properties listed above. Example configurations of the antenna, for which some of these properties were adjusted, were tested. These example configurations are illustrated in the following table:

| Property | Example 1 | Example 2 | Example 3 | Example 4 |
|---|---|---|---|---|
| Outer Diameter (OD) | 30 mm | 30 mm | 30 mm | 26 mm |
| # Turns (N) | 12 | 10 | 8 | 10 |
| Coil Pitch (P) | 1.0 mm | 1.0 mm | 1.0 mm | 1.0 mm |
| Trace Width (W) | 0.5 mm | 0.5 mm | 0.5 mm | 0.5 mm |
| Trace Thickness (T) | 1.4 mil | 1.4 mil | 1.4 mil | 1.4 mil |
| Coil Spacing (S) | 2 mil | 2 mil | 2 mil | 2 mil |
| Max. Power Delivery | 32.0 mW | 39.4 mW | 43.7 mW | 23.3 mW |

As shown in the above table, the maximum power delivered provided by each example coil configuration met or exceeded the 10-30 mW power requirement, even with the reduced coil outside diameter of Example 4.

The external controller 100 can have two components: power mat 110 and bedside control unit 120. Control unit 120 can be connected to power mat 110 by wire, for example, and is designed to be placed bedside, e.g., on a nightstand. The control unit can include a user interface, e.g., buttons, knobs, touchscreen, etc., to allow the user to control operation of the system when using the system in bed. Power mat 110 can be designed to be placed on the sleeping surface, such as a bed mattress, and therefore can be configured to have the form of a pad, e.g., a thin, flat, soft, flexible and non-slip configuration. Power mat 110 supports one or more wireless power transmit coils 112 in or on a flexible or semi-flexible surface 114. Power mat 110 can be positioned on the sleeping surface so that a lower edge 116 of the mat corresponds approximately to the position of the patient's shoulders while sleeping. The shape and size of the power mat 110 can correspond, for example, to that of a pillow, such as a queen size pillow.

Control unit 120 can excite power transmit coils 112 to generate an electromagnetic field. External controller 100 can utilize transmit coils 112 in power mat 110 to provide tethered wireless power transfer to stimulator 20 by way of receiving antenna 32 through electromagnetic induction. When the patient is in the sleeping position on the sleeping surface, antenna 32 of stimulator 20 can be positioned within the electromagnetic field produced by transmit coils 112 of power mat 110. The shape of the field can be tailored through the configuration of the coils 112 to provide a field that is optimized for powering the stimulator 20 through various sleeping positions. For example, the field can be configured extend horizontally (as viewed in FIGS. 10A-C) between the coils 112, so that the stimulator 20 can be powered any time it is positioned within the vertical bounds of the horizontally extending field.

Through induction, electric current can be induced in receiving antenna 32 and that current can be provided to stimulator electronics package 50. Components 52 in electronics package 50 control the operation of electrodes 82. Through this operation, electrodes 82 can be utilized as stimulating electrodes for applying electrical stimulation to nerves or muscles, for example; as EMG sensing electrodes, for example, for detecting a neuromuscular response, to the application of electrical stimulation; or as both stimulation and sensing electrodes at different times during the application of stimulation therapy.

In addition to providing power to stimulator 20, external controller 100 can also provide a data link for facilitating two-way communication between the controller and the stimulator. While powering the stimulator, controller 100 can simultaneously provide a wireless data signal that is used to program the stimulator with settings, such as electrode assignments and stimulation parameters, and also retrieve stored data from the stimulator, such as triggered stimulation events, measured EMG responses or other electrical physiological signals, current values, electrode impedances, and data related to the wireless power transfer between controller 100 and stimulator 20.

Additionally, the stimulator 20 can monitor the impedance and/or voltage of the stimulator antenna 32 so that the power supplied to the stimulator can be calculated. This can be provided as feedback to the controller 100 that allows the controller to adjust the current supplied to the power transmit coils 112. The controller 100 can control the power delivered to the stimulator so as to remain within the standards/requirements set forth above. At the same time, the feedback can also facilitate increasing the current supplied to the power transmit coils 112 so that adequate power transfer to the stimulator 20 is maintained, again within the prescribed limits. In this manner, the controller 100 can implement closed-loop control to optimize the power supplied to the stimulator 20.

The operation of the controller 100 can be controlled through the user interface 200, which allows the user, e.g., the patient, physician or other caretaker, to control aspects of the operation of the implantable stimulation system 10. The control can be local, e.g., by the patient using a user interface of the control unit 120 or the patient user interface 200, or remote, e.g., by the physician through internet/cloud 208. The control unit 120 can have a small footprint and power mat 110 can be flexible in design so that external controller 100 is small, discreet, and portable for travel purposes.

Power Mat Configuration

To account for varying sleeping positions throughout the night, power mat 110 can have a large enough footprint to allow patient movement while still maintaining the ability to transmit power to stimulator 20. At the same time, external controller 100 does produce electromagnetic radiation at a level that falls outside the guidelines for maximum permissible magnetic field exposure as recommended in IEEE Standard C95.1-2005 (Reference 3).

Figure 10A:
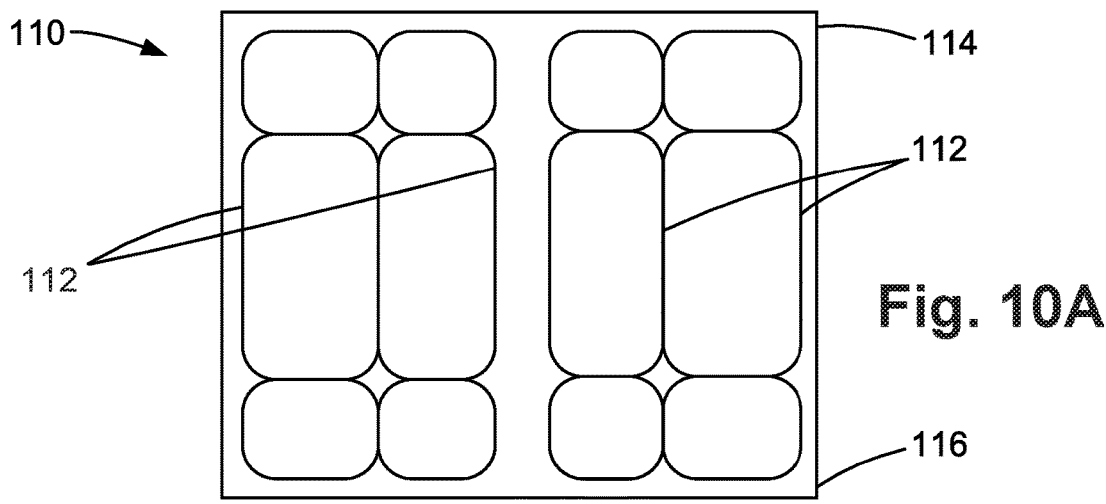
FIGS. 10A-10C are schematic illustrations depicting exemplary configurations of a power mat portion of an electrical stimulation system according to an aspect of the present invention.
Figure 10B:
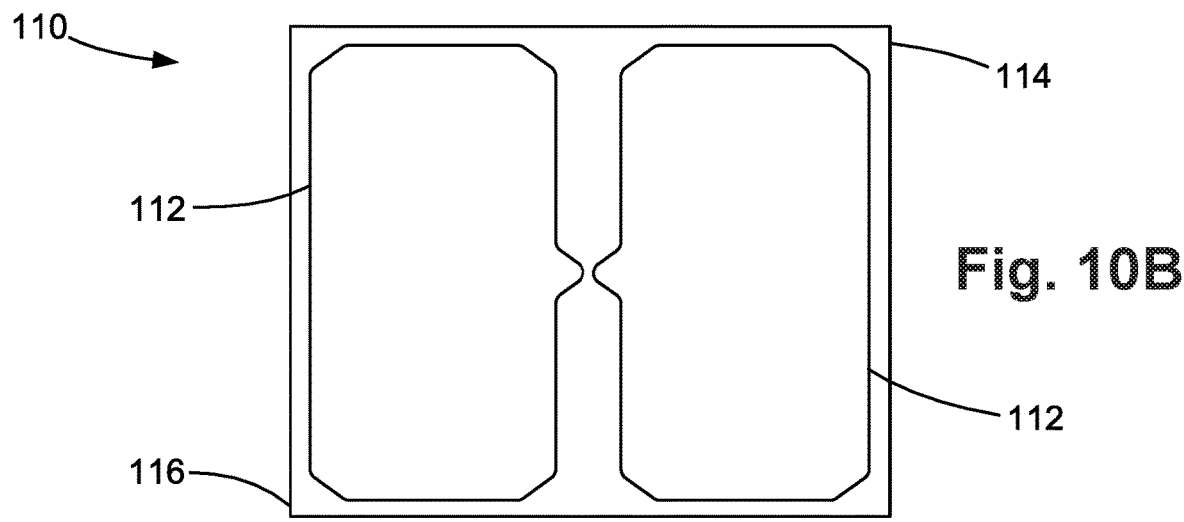
Figure 10C:
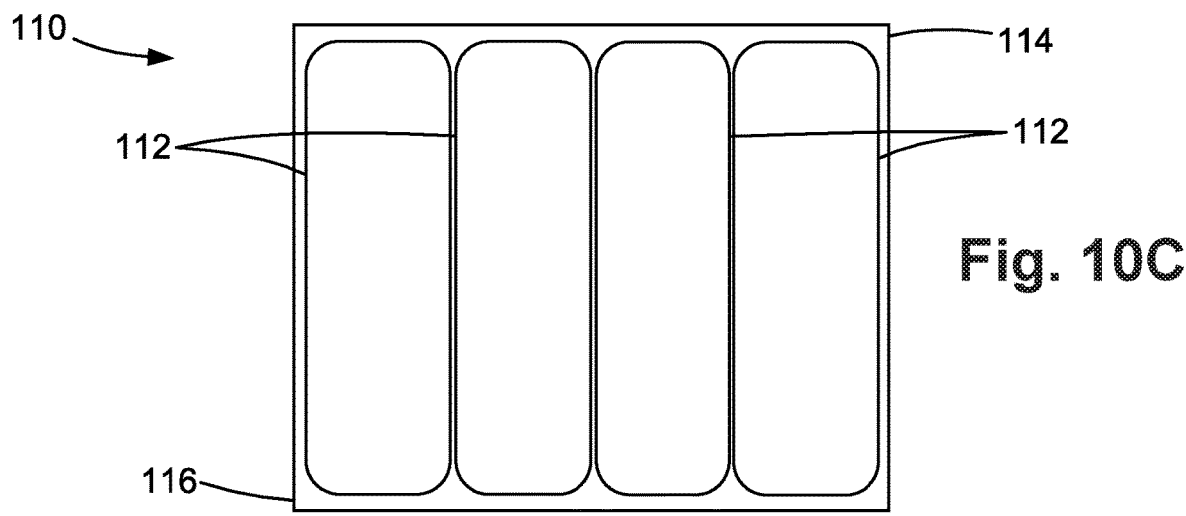

Example transmit coil configurations that can be implemented in power mat 110 are illustrated in FIGS. 10A-10C. These example transmit coil configurations can be implemented with a flex circuit design, i.e., the coils can be formed (e.g., etched) from a conductive metal (e.g., copper or gold) laminated on a flexible substrate (e.g., polyimide). The examples of FIGS. 10A-10C illustrate the overall shape of transmit coils 112 without showing the individual turns of the transmit coils. This is because the properties of the transmit coils 112, e.g., the number of turns, coil pitch/spacing, trace width, etc. is not limited, as can be the case with coils 34, 36 of antenna 32. Antenna coils 34, 36 can be tailored specifically for maximum induced power generation due to the small footprint limitations of antenna 32 of stimulator 20. Power mat 110 can be larger in comparison and transmit coils 112 can be free to be configured to produce a magnetic field that can be limited only by requiring a level that falls within the IEEE magnetic field exposure guidelines mentioned previously.

Accordingly, transmit coils 112 can be configured to maximize the space or volume that the magnetic field covers so as to allow for variations in the patient position during sleep. This can give the system the ability to continuously power the stimulator through a variety of sleeping positions throughout the night. FIG. 10A shows a twelve coil example configuration of transmit coils 112; FIG. 10B shows a two coil example configuration of transmit coils; and FIG. 10C shows a four coil example configuration of transmit coils. For all of these example configurations, experimental testing showed that transmit coils 112 are capable of meeting the system power requirements, within the IEEE exposure guidelines, while allowing for consistent power transfer to the antenna 32 over an effective volume of approximately 32×76×25 cm (L×W×H), which was found to be sufficient to cover the patient during a normal sleep cycle.

The twelve coil configuration of transmit coils 112 in FIG. 10A can allow for dynamic control of the magnetic field produced by the power mat 110. Through data coupling and communication between external controller 100 with stimulator 20, a determination can be made as to which coil(s) of the twelve coil configuration are effectuating the power coupling between the external controller and the stimulator. Through this determination, the external controller 100 can power only those coils necessary to power stimulator 20, given the current position of the patient relative to power mat 110. As the patient changes positions, the stimulator can detect any decrease in power transmission, which can trigger a reassessment and the selection of different coil(s). This configuration can thus be self-tuning, on-the-fly to maximize the electromagnetic field produced by the power mat 110 in the area of the antenna 32.

The two coil configuration of the transmit coils 112 in FIG. 10B can be static power coils that produce a continuous electromagnetic field around power mat 110. This configuration can be tuned to maximize the electromagnetic field strength in the largest possible volume so that power transmission is maximized throughout a wide variety of patient positions.

In the example configurations of both FIG. 10A and FIG. 10B, power mat 110 can have a flexible construction facilitated by a flexible circuit construction of transmit coils 112 housed within a flexible cover, such as, for example, soft plastic, rubber, fabric, etc. Transmit coils 112 can, for example, have a flexible PCB construction similar to antenna 32 of stimulator 20. For instance, transmit coils 112 can be constructed as a single layer flexible PCB, with conductive traces etched from copper, for example, laminated on a polyimide, for example, substrate.

Each of the disclosed aspects and embodiments of the present disclosure may be considered individually or in combination with other aspects, embodiments, and variations of the disclosure. Further, while certain features of embodiments and aspects of the present disclosure may be shown in only certain figures or otherwise described in the certain parts of the disclosure, such features can be incorporated into other embodiments and aspects shown in other figures or other parts of the disclosure. Along the same lines, certain features of embodiments and aspects of the present disclosure that are shown in certain figures or otherwise described in certain parts of the disclosure can be optional or deleted from such embodiments and aspects. Additionally, when describing a range, all points within that range are included in this disclosure. Furthermore, all references cited herein are incorporated by reference in their entirety.

What is claimed is:

1. A neuromodulation system comprising:
   a neuromodulation device comprising:
      a neuromodulation lead comprising:
         a lead body with a right portion, a left portion, and an intermediate portion;
         a plurality of electrodes comprising a left set of electrodes disposed on the left portion of the lead body and a right set of electrodes disposed on the right portion of the lead body, at least one of the plurality of electrodes being a stimulating electrode configured to deliver a stimulation signal to a target site, the lead body biased towards a substantially omega shape when the neuromodulation lead is fully deployed and/or the intermediate portion of the lead body biased towards an inferior position relative to the left and right electrode sets when the neuromodulation lead is fully deployed;
      an antenna operably coupled to the neuromodulation lead configured to produce an induced current in response to being disposed in an electromagnetic field and comprising an upper and a lower coil electrically connected to each other in parallel;
   an electronics package comprising electrical components to control the application of a stimulation signal via the stimulating electrode;
   an external controller comprising a control unit and a power mat that supports one or more power transmission coils that are excitable to produce an electromagnetic field for inducing electrical current in the antenna to power the neuromodulation lead;
   a sensor configured to be implantable adjacent to an anterior lingual muscle and configured to record physiological data; and
   a computing device comprising:
      a non-transitory memory storing instructions; and
      a processor to access the non-transitory memory and execute the instructions to at least:
         monitor the physiological data recorded by the sensor;

identify a trigger within the physiological data, wherein the trigger is identified as a biomarker for a condition related to sleep; and apply a rule-based classification to the trigger to determine whether one or more parameters of the stimulation signal should be altered based on the biomarker, the stimulating electrode configured to deliver the stimulation signal to the target site during a period and to alter the one or more parameters of the stimulation signal in response to a signal from the computing device.

2. The neuromodulation system of claim 1, wherein the target site is the hypoglossal nerve.

3. The neuromodulation system of claim 1, wherein the location of the left and right set of electrodes on the respective left and right portion of the lead body is based on the location of a respective left and right stimulation target site comprising the hypoglossal nerve trunk, distal branches of the hypoglossal nerve, nerve branches that innervate horizontal fibers within the genioglossus muscle, nerve branches that innervate oblique fibers within the genioglossus muscle, or any suitable combination thereof when the neuromodulation lead is fully deployed.

4. The neuromodulation system of claim 1, wherein the electronics package is located on the neuromodulation device and the antenna is configured to supply electrical current to the electronics package to power the electronics package.

5. The neuromodulation system recited in claim 1, further comprising a user interface configured to communicate with the neuromodulation device so that operation of the neuromodulation device can be controlled, at least in part, via the user interface.

6. The neuromodulation system of claim 1, wherein the antenna comprising a substrate having an upper surface and a lower surface, the upper coil comprising a plurality of coil turns disposed on the upper surface of the substrate, and the lower coil comprising a plurality of coil turns disposed on the lower surface of the substrate, wherein the upper and lower coils are electrically connected to each other in parallel.

7. The neuromodulation system of claim 6, wherein the antenna is constructed from a flexible circuit board, the upper and lower coils being etched from conductive layers on the substrate, wherein the electronics package comprises one or more electronic components mounted on a portion of the flexible circuit board, wherein the flexible circuit board is configured to electrically connect the one or more electronic components to the antenna.

8. The neuromodulation system of claim 6, wherein the antenna further comprises a plurality of connectors that extend through the substrate and electrically connect the upper coil to the lower coil.

9. The neuromodulation system of claim 8, wherein the upper and the lower coils are configured to overlie each other to position coil turns overlying each other, and wherein the connectors are configured to interconnect overlying coil turns of the upper and lower coils.

10. The neuromodulation system of claim 1, wherein the sensor is an EMG sensing electrode and is at least one of the plurality of electrodes disposed on the neuromodulation lead.

11. The neuromodulation system of claim 1, wherein the rule-based classification is adaptive.

12. The system of claim 1, wherein the physiological data comprises phasic activity of the genioglossus muscle, tonic activity of the genioglossus muscle, or both.

13. The system of claim 1, wherein the physiological data is obtained from EMG activity from the musculature of the anterior airway.

14. The system of claim 1, wherein the physiological data is EMG characteristic signals that correlate to respiration, sleep position during sleep, sleep state, or combinations thereof.

15. The system of claim 1, wherein the trigger comprises a change in at least one parameter of the physiological data.

16. The system of claim 1, wherein the trigger indicates a change in body position.

17. The system of claim 1, wherein the trigger indicates a change in phasic and/or tonic genioglossus muscle activity during respiration.

18. The system of claim 1, wherein the biomarker is related to a stage in a sleep cycle, wherein the stage in the sleep cycle is awake, non-REM stage 1 light sleep, non-REM stage 2 light sleep, non-REM stage 3 deep sleep, REM sleep, or combinations thereof.

19. The system of claim 1, wherein initial rules of an algorithm used by the rule-based classification are determined based on historical values for a population, historical values for a patient, and/or patient derived values.

* * * * *

UNITED STATES PATENT AND TRADEMARK OFFICE
CERTIFICATE OF CORRECTION

PATENT NO. : 11,291,842 B2
APPLICATION NO. : 16/866523
DATED : April 5, 2022
INVENTOR(S) : Anthony V. Caparso et al.

It is certified that error appears in the above-identified patent and that said Letters Patent is hereby corrected as shown below:

In the Claims

Column 23, Claim 5, Line 29, delete "recited in" and insert -- of --, therefor.

Column 24, Claim 12, Line 20, delete "system" and insert -- neuromodulation system --, therefor.

Column 24, Claim 13, Line 23, delete "system" and insert -- neuromodulation system --, therefor.

Column 24, Claim 14, Line 26, delete "system" and insert -- neuromodulation system --, therefor.

Column 24, Claim 15, Line 30, delete "system" and insert -- neuromodulation system --, therefor.

Column 24, Claim 16, Line 32, delete "system" and insert -- neuromodulation system --, therefor.

Column 24, Claim 17, Line 34, delete "system" and insert -- neuromodulation system --, therefor.

Column 24, Claim 18, Line 37, delete "system" and insert -- neuromodulation system --, therefor.

Column 24, Claim 19, Line 42, delete "system" and insert -- neuromodulation system --, therefor.

Signed and Sealed this
Twenty-first Day of June, 2022

Katherine Kelly Vidal
*Director of the United States Patent and Trademark Office*